United States Patent
Xiao et al.

(10) Patent No.: US 12,214,310 B2
(45) Date of Patent: Feb. 4, 2025

(54) SYSTEMS AND METHODS FOR OXYGEN PRODUCTION

(71) Applicant: QINGDAO KINGON MEDICAL SCIENCE AND TECHNOLOGY CO., LTD., Shandong (CN)

(72) Inventors: Wu Xiao, Qingdao (CN); Bang An, Qingdao (CN); Changpeng Chu, Qingdao (CN); Benrong Zhang, Qingdao (CN); Mingshan Wang, Qingdao (CN); Yujie Li, Qingdao (CN)

(73) Assignee: QINGDAO KINGON MEDICAL SCIENCE AND TECHNOLOGY CO., LTD., Qingdao (CN)

( * ) Notice: Subject to any disclaimer, the term of this patent is extended or adjusted under 35 U.S.C. 154(b) by 609 days.

(21) Appl. No.: 17/304,946

(22) Filed: Jun. 29, 2021

(65) Prior Publication Data

US 2021/0322918 A1      Oct. 21, 2021

Related U.S. Application Data

(63) Continuation of application No. PCT/CN2018/125746, filed on Dec. 29, 2018.

(51) Int. Cl.
*B01D 53/04*     (2006.01)
*A61M 16/00*    (2006.01)
(Continued)

(52) U.S. Cl.
CPC ......... *B01D 53/04* (2013.01); *A61M 16/0003* (2014.02); *A61M 16/201* (2014.02);
(Continued)

(58) Field of Classification Search
CPC .............. B01D 53/04; B01D 2253/108; B01D 2256/12; B01D 2259/40007;
(Continued)

(56) References Cited

U.S. PATENT DOCUMENTS 4,916,630 A * 4/1990 Miller .................... G01N 30/00
702/30
5,048,515 A * 9/1991 Sanso ............... A61M 16/0051
128/204.26
(Continued)

FOREIGN PATENT DOCUMENTS

CN     101049527 A    10/2007
CN     102120054 A     7/2011
(Continued)

OTHER PUBLICATIONS

First Office Action in Chinese Application No. 201880100288.6 mailed on Jul. 27, 2022, 24 pages.
(Continued)

*Primary Examiner* — Stephen Hobson
(74) *Attorney, Agent, or Firm* — METIS IP LLC

(57) ABSTRACT

An oxygen production system (100) may include a main control module (120) and a molecular sieve module (140). The molecular sieve module (140) may include a molecular sieve and a molecular sieve information unit. The molecular sieve information unit may be configured to store information of the molecular sieve. The main control module (120) may be configured to read, write and/or update the information of the molecular sieve stored in the molecular sieve information unit. When reading, in response to at least part of the information of the molecular sieve exceeding a preset range, the main control module (120) may control the oxygen production system (100) to perform a corresponding operation. The oxygen production system (100) may occupy small space, have good performance and a high oxygen production efficiency, and enable a user to obtain a more user-friendly experience.

18 Claims, 10 Drawing Sheets

(51) Int. Cl.
*A61M 16/20* (2006.01)
*G06N 3/08* (2023.01)
*G16H 10/00* (2018.01)
*G16H 40/60* (2018.01)

(52) U.S. Cl.
CPC ............... *G06N 3/08* (2013.01); *G16H 10/00* (2018.01); *G16H 40/60* (2018.01); *A61M 2016/0015* (2013.01); *A61M 2202/0208* (2013.01); *B01D 2253/108* (2013.01); *B01D 2256/12* (2013.01)

(58) Field of Classification Search
CPC .. B01D 2259/40009; B01D 2259/4533; B01D 53/047; B01D 53/053; A61M 16/0003; A61M 16/201; A61M 2016/0015; A61M 2202/0208; A61M 16/0677; A61M 2016/0021; A61M 2205/3365; A61M 2205/3553; A61M 16/0051; A61M 16/204; A61M 16/202; A61M 16/0063; A61M 16/208; A61M 2016/0027; A61M 2016/1025; A61M 2205/276; A61M 2205/332; A61M 2205/3368; A61M 2205/3592; A61M 2205/3606; A61M 2205/362; A61M 2205/52; A61M 2205/581; A61M 2205/582; A61M 2205/6009; A61M 2205/6072; A61M 2205/609; A61M 2205/7545; A61M 2205/8206; A61M 2205/8237; A61M 2230/06; A61M 2230/205; A61M 16/101; A61M 2205/502; A61M 2230/30; A61M 2230/40; A61M 2230/63; A61M 16/024; G06N 3/08; G16H 10/00; G16H 40/60; G16H 20/40; C01B 13/0259; G05D 11/13
See application file for complete search history.

(56) References Cited

U.S. PATENT DOCUMENTS

| | | | | |
|---|---|---|---|---|
| 5,165,397 A | * | 11/1992 | Arp | A61M 16/0051 128/204.26 |
| 9,675,925 B2 | * | 6/2017 | Ramkumar | B01D 53/0476 |
| 2002/0096174 A1 | * | 7/2002 | Hill | B01D 53/0476 128/204.22 |
| 2002/0121191 A1 | * | 9/2002 | Warren | B01D 53/047 95/96 |
| 2002/0195105 A1 | * | 12/2002 | Blue | A61M 16/024 128/205.25 |
| 2007/0023039 A1 | * | 2/2007 | Ishizaki | A61M 16/101 128/201.21 |
| 2007/0221225 A1 | * | 9/2007 | Kutt | A63B 23/18 128/204.23 |
| 2008/0241052 A1 | * | 10/2008 | Hooper | B01D 53/0476 96/108 |
| 2009/0065007 A1 | * | 3/2009 | Wilkinson | A61M 16/0069 96/108 |
| 2010/0051030 A1 | * | 3/2010 | Richard | A61M 16/101 128/204.23 |
| 2010/0095841 A1 | * | 4/2010 | Naheiri | B01D 53/0476 95/96 |
| 2010/0242734 A1 | * | 9/2010 | Maeda | C01B 13/0259 96/110 |
| 2011/0232483 A1 | * | 9/2011 | Haberland | A61M 16/0672 96/110 |
| 2012/0291884 A1 | * | 11/2012 | Yamaura | B01D 53/0454 137/455 |
| 2015/0231551 A1 | * | 8/2015 | Wilkinson | A61M 16/101 128/203.14 |
| 2015/0273174 A1 | * | 10/2015 | Hart | A61M 16/101 128/202.13 |
| 2016/0030699 A1 | * | 2/2016 | Zapol | A61M 16/10 128/202.26 |
| 2016/0184772 A1 | * | 6/2016 | White | B01D 53/02 96/10 |
| 2016/0340197 A1 | * | 11/2016 | Zones | B01J 29/70 |
| 2017/0072159 A1 | * | 3/2017 | Romano | A61M 16/0003 |
| 2017/0304767 A1 | * | 10/2017 | Byrd | B01D 53/0454 |
| 2023/0330359 A1 | * | 10/2023 | Scholz | B01F 23/237 |
| 2024/0050484 A1 | * | 2/2024 | Liu | A61K 9/0024 |

FOREIGN PATENT DOCUMENTS

| | | |
|---|---|---|
| CN | 102120055 A | 7/2011 |
| CN | 102266616 A | 12/2011 |
| CN | 202325849 U | 7/2012 |
| CN | 202625849 U | 12/2012 |
| CN | 103288054 A | 9/2013 |
| CN | 103398744 A | 11/2013 |
| CN | 103693624 A | 4/2014 |
| CN | 103847632 A | 6/2014 |
| CN | 204111315 U | 1/2015 |
| CN | 104503264 A | 4/2015 |
| CN | 104906671 A | 9/2015 |
| CN | 204897398 U | 12/2015 |
| CN | 106039607 A | 10/2016 |
| CN | 106044719 A | 10/2016 |
| CN | 205814814 U | 12/2016 |
| CN | 107297109 A | 10/2017 |
| CN | 107362425 A | 11/2017 |
| CN | 107572482 A | 1/2018 |
| CN | 107670152 A | 2/2018 |
| CN | 107866012 A | 4/2018 |
| CN | 207216400 | 4/2018 |
| CN | 108563153 A | 9/2018 |
| JP | 2001029473 A | 2/2001 |
| JP | 2006006521 A | 1/2006 |
| JP | 2008136658 A | 6/2008 |
| JP | 2014124342 A | 7/2014 |
| KR | 20070106964 A | 11/2007 |
| WO | 2012089093 A1 | 7/2012 |
| WO | 2018021560 A1 | 2/2018 |

OTHER PUBLICATIONS

International Search Report in PCT/CN2018/125746 mailed on Sep. 19, 2019, 8 pages.
Written Opinion in PCT/CN2018/125746 mailed on Sep. 19, 2019, 10 pages.

\* cited by examiner

SYSTEMS AND METHODS FOR OXYGEN PRODUCTION

CROSS-REFERENCE TO RELATED APPLICATIONS

This application is a continuation of International Application No. PCT/CN2018/125746, filed on Dec. 29, 2018, the content of which is hereby incorporated by reference.

TECHNICAL FIELD

The present disclosure generally relates to medical devices, in particular, relates to oxygen production systems and methods.

BACKGROUND

With the improvement of people's living standards and awareness of health demand, oxygen inhalation is gradually become a fashion for family health. Home oxygen production machines can be divided into an electron oxygen generator, a molecular sieve oxygen generator, a chemical oxygen generator, and an oxygen-enrichment oxygen generator according to a working principle. Currently, the molecular sieve oxygen generator is a uniquely mature oxygen generator that satisfies an international standard and a national standard. There are still many improvable things of the current oxygen generator, especially a portable oxygen generator. Therefore, it is necessary to provide an improved oxygen production system and method that allows a user to get a better experience.

SUMMARY

One aspect of the present disclosure provides an oxygen production system including a main control module and a molecular sieve module. The molecular sieve module may include a molecular sieve and a molecular sieve information unit. The molecular sieve information unit may be configured to store information of the molecular sieve. The main control module may be configured to read, write, and/or update the information of the molecular sieve stored in the molecular sieve information unit. In response to at least a part of the information of the molecular sieve exceeding a preset range, the main control module may control the oxygen production system to perform a corresponding operation.

In some embodiments, the information of the molecular sieve may include at least one of design lifetime information, accumulated run time, temperature information, operation state information, altitude information, or position information of the molecular sieve.

In some embodiments, the main control module may be also configured to update at least one of the accumulated run time, the temperature information, the operation state information, the altitude information, or the position information, and write the updated information into the molecular sieve information unit. The main control module may update the accumulated run time according to a run time of each run of the molecular sieve.

In some embodiments, the molecular sieve module may store official information of the molecular sieve in the molecular sieve information unit when the molecular sieve module leaves the factory, and the official information may include at least one of a unique official identification or other official information. The main control module may be configured to read the at least one of the identification information or other information of the molecular sieve from the molecular sieve information unit. The main control module may control the oxygen production system to stop running and/or perform a reminding operation, in response to at least one of the following situations including the identification information of the molecular sieve is not read; identification information of the molecular sieve read by the main control module does not match the unique official identification; the identification information of the molecular sieve read by the main control module matches the unique official identification, but the other information of the molecular sieve does not match the other official information.

In some embodiments, the molecular sieve information unit may include at least one of following storage devices: an electrically erasable programmable read and write memory, a radio frequency memory, a wireless memory, an optical disk, and a magnetic disk.

In some embodiments, the information of the molecular sieve may be encrypted and stored in the molecular sieve information unit.

In some embodiments, the oxygen production system may further include a gas tank, a gas ejection port, and a respiration sensor. The respiration sensor may be configured to detect a user's breath. An oxygen transport pipeline may be provided between the gas tank and the gas ejection port. The respiration sensor may be connected to the oxygen transport pipeline through a bypass pipeline.

In some embodiments, a joint between the oxygen transport pipeline and the bypass pipeline may be provided with a two-position three-way valve. The two-position three-way valve may be connected to the gas ejection port and the respiration sensor at the initial moment when the oxygen production system is started. The main control module may also be configured to control a connecting state of the two-position three-way valve. In response to the respiration sensor detecting the user's inhalation, the main control module may control the two-position three-way valve to connect the gas tank and the gas ejection port, and maintain the connection between the gas tank and the gas ejection port for a preset time. After the preset time, the main control module may control the two-position three-way valve to connect the gas ejection port and the respiration sensor.

In some embodiments, the bypass pipeline may be provided with a one-way valve; the main control module may also be configured to, control the one-way valve to connect the bypass pipeline with the atmosphere to discharge gas in the bypass pipeline after the preset time, or, in response to pressure at the respiration sensor exceeding a preset pressure threshold, control the one-way valve to connect the bypass line with the atmosphere to discharge the gas in the bypass line.

In some embodiments, the oxygen supply pipeline may be provided with an oxygen supply valve for conducting or blocking the oxygen supply pipeline. The gas ejection port may be provided with a pressure sensor for detecting pressure at the gas ejection port.

In some embodiments, the respiration sensor and the pressure sensor may be the same sensor.

In some embodiments, the main control module may also be configured to control the oxygen supply valve to be turned on before a formal oxygen ejection so that the gas tank outputs a preset amount of oxygen to the gas ejection port. After the gas tank outputs the preset amount of oxygen to the gas ejection port, in response to the pressure sensor detecting that the pressure at the gas ejection port exceeds the preset pressure threshold, the main control module may control the oxygen supply valve to block the oxygen supply pipeline to stop oxygen ejection. In response to the pressure sensor detecting that the pressure at the gas ejection port does not exceed the preset pressure threshold, the main control module may control the oxygen supply valve to continue to be turned on to perform the formal oxygen ejection.

In some embodiments, the bypass line is provided with a bypass valve for conducting or blocking the bypass pipeline. During an oxygen ejection, the main control module may control the oxygen supply valve to be turned on to conduct the oxygen supply pipeline, and the bypass valve may block the bypass pipeline. At the end of an oxygen supply, the main control module may control the oxygen supply valve to block the oxygen supply pipeline. At the same time, in response to the pressure sensor detecting that the pressure at the gas ejection port exceeds the preset pressure threshold, the main control module may control the bypass valve to continue blocking the bypass pipeline. In response to the pressure sensor detecting that the pressure at the gas ejection port does not exceed the preset pressure threshold, the main control module may control the bypass valve to be turned on so that the respiration sensor detects the user's breath.

In some embodiments, the molecular sieve may be connected with at least one valve. The molecular sieve and the at least one valve may be integrated in the molecular sieve module. The molecular sieve and the at least one valve may be integrally replaced.

In some embodiments, the oxygen production system may further include a temperature sensor configured to detect the temperature of the molecular sieve. The temperature sensor may be integrated in the molecular sieve. The oxygen production system may further include a cooling fan configured to dissipate heat for the molecular sieve. The main control module may also be configured to control the oxygen production system according to the temperature of the molecular sieve. In response to the temperature of the molecular sieve exceeding a first preset threshold, the main control module may control the cooling fan to increase a rotation speed. In response to the temperature of the molecular sieve being lower than a second preset threshold, the main control module may control the cooling fan to reduce the rotation speed.

In some embodiments, the main control module may further be configured to in response to the temperature of the molecular sieve exceeding a third preset threshold or lower than a fourth preset threshold, control the oxygen production system to stop running.

In some embodiments, the oxygen production system may further include at least one of a respiration sensor, an acceleration sensor, an altitude sensor, or a pressure sensor. The respiration sensor may be configured to detect a respiratory frequency and/or a respiratory state of the user. The acceleration sensor may be configured to detect a motion state of the user. The altitude sensor may be configured to detect an altitude of the oxygen production system. The pressure sensor may be configured to detect the pressure in the gas tank of the oxygen production system. The main control module may also be configured to adjust at least one of an oxygen output flow or an oxygen output time according to at least one of the respiratory rate, the respiratory state, and the motion state of the user, the altitude, or the pressure in the gas tank. The at least one of oxygen output flow or the oxygen output time may be determined by at least one of artificial intelligence, machine recognition, or cloud processing methods. The artificial intelligence method may be implemented by a neural network model. An input of the neural network model may include at least one of the respiratory rate, the respiratory state, and the motion state of the user, the altitude, or the pressure in the gas tank, and an output of the neural network model may include at least one of the oxygen output flow or the oxygen output time.

In some embodiments, the oxygen production system may further include a gas ejection port for ejecting oxygen and a respiration sensor for detecting the respiratory state of the user. In response to the respiration sensor detecting an end of the user's exhalation, the main control module may control the gas ejection port to eject a preset amount of oxygen.

In some embodiments, the oxygen production system may further include a storage module for storing the user's respiratory state information and/or usage record.

Another aspect of the present disclosure provides a mask that includes an oxygen production system as previously described.

Another aspect of the present disclosure provides an oxygen production method. The method may include acquiring information of the molecular sieve in the oxygen production system; and in response to at least part of the molecular sieve information exceeding a preset range, controlling the oxygen production system to perform a corresponding operation.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
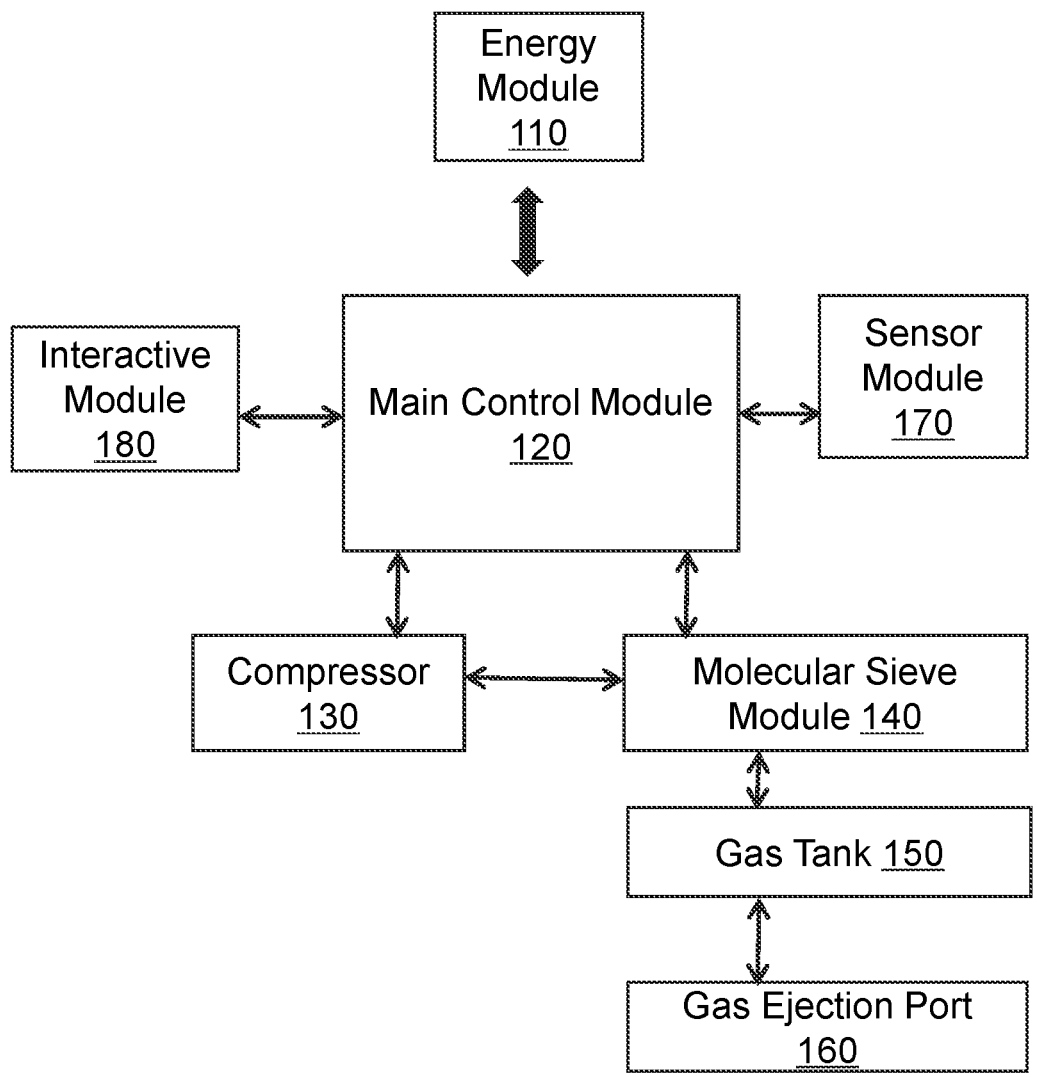
FIG. 1 is a schematic diagram illustrating an exemplary oxygen production system according to some embodiments of the present disclosure.

In order to illustrate the technical solutions related to the embodiments of the present disclosure, a brief introduction of the drawings referred to in the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

As used in the disclosure and the appended claims, the singular forms "a," "an," and "the" include plural referents unless the content clearly dictates otherwise. Generally speaking, the terms "comprising" and "including" only indicate that the steps and elements that have been clearly identified are included, these steps and elements do not constitute an exclusive list, and the method or device may also include other steps or elements.

While the present disclosure makes various references to certain modules or units in the system of the embodiment of the present disclosure, any number of different modules or units may be used and run on the client and/or server. The modules are merely illustrative, and different modules may be used in different aspects of the systems and methods.

The flowchart is used in the present disclosure to illustrate operations performed by the system according to some embodiments of the present disclosure. It should be understood that the preceding or following operations are not necessarily performed exactly in order. Instead, various steps may be processed in reverse or simultaneously. Besides, one or more other operations may be added to these processes, or one or more operations may be removed from these processes.

In order to explain the technical solutions of the embodiments of the present disclosure more clearly, the drawings required for the description of the embodiments will be briefly introduced below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

FIG. 1 is a schematic diagram illustrating an exemplary oxygen production system according to some embodiments of the present disclosure. The oxygen production system 100 may include an energy module 110, a main control module 120, a compressor 130, a molecular sieve module 140, a gas tank 150, a gas ejection port 160, a sensor module 170, and an interactive module 180.

The energy module 110 may be configured to provide energy (e.g., electrical energy) to other modules in the oxygen production system 100. In some embodiments, the energy module 110 may acquire electrical energy through an external power source. In some embodiments, the energy module 110 may provide electrical energy through an energy storage device, a power generation device, or a combination thereof. In some embodiments, the energy storage device may include one or more batteries. In some embodiments, the energy storage device may be charged by an external power source or by the power generation device. In some embodiments, the power generation device may include one or more electric generators. In some embodiments, the electric generator may employ one or more energy conversion devices of a human energy generation device, a light energy generation device, a thermal conductivity energy generation device, a wind energy generation device, and a nuclear energy generation device. In some embodiments, the energy module 110 may include an energy source management unit for managing an energy output of the energy module 110 and effectively assigning energy to each module and/or component in the oxygen production system 100. In some embodiments, when the energy module 110 acquires electrical energy through an external alternating current power source, the energy module 110 may also include a power adapter for converting the external alternating current into a direct current power applicable to the oxygen production system 100.

The main control module 120 may be configured to control other modules of the oxygen production system 100 to implement a function of the oxygen production system 100. In some embodiments, a controlling method may be a centralized type or a distributed type, and may be a wired type or a wireless type. In some embodiments, the main control module 120 may execute program instructions in the form of one or more processors. In some embodiments, the main control module 120 may receive data and/or information transmitted by the energy module 110, the compressor 130, the molecular sieve module 140, the sensor module 170, and the interactive module 180, and determine and control an operation of the oxygen production system 100 through a preset logic based on the information. In some embodiments, the main control module 120 may send instructions to the energy module 110, the compressor 130, the molecular sieve module 140, the sensor module 170, and the interactive module 180. For example, the main control module 120 may acquire the data and/or information transmitted by the molecular sieve module 140 (e.g., factory information, operation information, etc.) of the molecular sieve, process the data and/or information, and determine a molecular sieve state according to a processing result. Specifically, the main control module 120 may compare the data and/or information with a preset threshold. If the data and/or information is above or below the preset threshold, it may indicate that the molecular sieve state is abnormal. As another example, the main control module 120 may process the data and/or information by a state determination model. The state determination model may be a neural network model that is trained using data and/or information of a known molecular sieve and a state of the known molecular sieve. An input of the model may be the data and/or information of the molecular sieve, and an output of the model may be the state of the molecular sieve. The trained model may obtain the state of the molecular sieve according to new data and/or information. If the processing result indicates that the molecular sieve state is normal, the oxygen production system 100 may be controlled to operate normally. If the processing result indicates that the molecular sieve state is abnormal, the oxygen production system 100 may be controlled to operate in a safe mode or make an alarm. As another example, the main control module 120 may acquire data and/or information transmitted by the sensor module 160, process the data and/or information, and determine a current environment of the oxygen production system 100 and/or a current physiological state of a user according to the processing result. The main control module 120 may then adjust an operating parameter of the oxygen production system 100 (e.g., an oxygen output flow and/or an oxygen output time). Specifically, an adjustment rule of an operation parameter may be preset. Different environments and/or user physiological states may correspond to different operation parameters. The main control module 120 may adjust the operation parameter of the oxygen production system 100 according to the preset adjustment rule of the operation parameter. In some embodiments, the main control module 120 may adjust the operation parameter of the oxygen production system 100 by running a parameter adjustment model. The parameter adjustment model may be a neural network model that is trained using data relating to a known environment and/or a user physiological state, and the operation parameter. An input of the model may be the environment and/or the user physiological state, and an output of the model may be the operation parameter. Further, the adjustment rule of the operation parameter may be customized according to usage habits of different users, or an individualized operation parameter adjustment model may be trained according to historical usage records of the user. The main control module 120 may control the interactive module 180 to display the operation parameter of the oxygen production system 100, or display a user operation interface. The main control module 120 may also receive an operation instruction input by the user through the interactive module 180, and control the operation of the oxygen production system 100 according to the operation instruction. In some embodiments, the main control module 120 may include one or more sub-controllers (e.g., a single core processing device or a multi-core processing device). Merely by way of example, a driving controller may include an electronic control unit (ECU), a dedicated integrated circuit (ASIC), a dedicated instruction processor (ASIP), a graphics processor (GPU), a physical processor (PPU), a digital signal processor (DSP), a field-programmable gate array (FPGA), an editable logic circuit (PLD), a microcontroller unit, a reduced instruction set computer (RISC), a microprocessor, or the like, or any combination of thereof.

The compressor 130 may be used to compress air. In some embodiments, a gas inlet port of the compressor 130 may be connected to an air filter, and the air may be filtered and then entered the compressor 130. The compressor 130 may be various types of air compressors, including but not limited to, a centrifugal air compressor, a piston air compressor, a rolling piston air compressor, a slide air compressor, a vortex air compressor, a screw air compressor, or the like. In some embodiments, the compressor 130 may use a frequency conversion compression air pump, and the user may adjust an output power of the frequency conversion compression air pump according to requirements. In some embodiments, the gas inlet port of the compressor 130 may also be connected to an air detection sensor that is configured to detect air quality. In some embodiments, the oxygen production system 100 may perform a reminding operation when the air quality does not reach a preset request. For example, the air quality may be measured by an air quality index (AQI). When the AQI exceeds a preset threshold (e.g., 300, 250, 200, 150, 100, etc.), the oxygen production system 100 may perform the reminding operation. In some embodiments, the main control module 120 may control the interactive module 180 to perform the reminding operation. For example, the main control module 120 may control the interactive module 180 to display alarm information, issue an alarm sound, light an alarm lamp, or the like. As another example, reminding information may be sent to a user terminal (e.g., a mobile phone, a computer, etc., of the user) through a communication module (not shown in figures) of the oxygen production system 100.

The molecular sieve module 140 may be used to separate oxygen from air. The molecular sieve module 140 may include at least one molecular sieve adsorption tower for adsorbing nitrogen in compressed air, so that oxygen is reserved in the gas phase, thereby separating nitrogen and oxygen to acquire the desired oxygen. In some embodiments, the molecular sieve module 140 may include a double molecular sieve tower. In some embodiments, a valve (e.g., an equalizing valve, a throttle valve) may be used to establish a connection between the double molecular sieve tower. The double molecular sieve tower may be connected to the compressor 130 and/or the gas tank 150 through the valve. In some embodiments, the valve may be integrated into the molecular sieve module 140. The double molecular sieve tower and the valve may be provided to the user as a whole, and may be integrally replaced. In some embodiments, the molecular sieve module 140 may also include a molecular sieve information unit for storing molecular sieve information, such as factory information and operation information.

The gas tank 150 may store oxygen produced by the molecular sieve module 140. The gas tank 150 may be connected to an air outlet of the molecular sieve module 140 through the valve. The gas tank 150 may also be connected to the gas ejection port 160 through the valve. In some embodiments, the gas tank 150 may be a wet-type gas tank. In some embodiments, the gas tank 150 may be a dry-type gas tank, including but not limited to, an oil-sealed gas tank, a grease-sealed gas tank, a flexible film sealed gas tank, or the like. The gas ejection port 160 may be configured to eject oxygen and provide the oxygen to the user.

The sensor module 170 may be configured to detect an environmental condition of the oxygen production system 100 and/or a current physiological state of the user. The sensor module 170 may convert the detected environmental condition and/or the physiological state of the user into an electrical signal. In some embodiments, a sensor for detecting the environmental condition of the oxygen production system 100 may include an altitude sensor, a temperature sensor, a pressure sensor, an oxygen concentration sensor, or the like. In some embodiments, the sensor for detecting the current physiological state of the user may include a respiratory sensor, a blood oxygen concentration sensor, a blood pressure sensor, a pulse sensor, a heart rate sensor, a speed sensor, an acceleration sensor, or the like.

The interactive module 180 may be configured to interact with the user. In some embodiments, the interactive module 180 may have a display function, which may display an operation parameter of the oxygen production system 100 and/or an item that may be operated by the user. In some embodiments, the interactive module 180 may have a speech broadcast function. For example, an operation state of the oxygen production system 100 may be broadcast, or when the oxygen production system 100 is abnormal, an abnormal condition may be broadcast. Specifically, a speaker, a buzzer, or the like, may be integrated into the interactive module 180. In some embodiments, the interactive module 180 may have a luminescent function. For example, when an exception occurs in the oxygen production system 100, the interactive module 180 may glow or twinkle. Specifically, a light-emitting diode, or the like, may be integrated into the interactive module 180. The user may operate through the interactive module 180. The user operation may include, but is not limited to, touching, pressing a button, clicking, handwriting, a voice control, a body control, or the like. In some embodiments, the interactive module 180 may have an identification function that identifies an identity of the operator. For example, only when the operator passes an authentication, the operation of the user may be accepted by the oxygen production system 100. Various techniques may be employed, such as a secret key technique and a biometric identification technique. The biometric identification technique may include, but is not limited to, a fingerprint recognition, an iris recognition, a vein recognition, a sound recognition, a face recognition, or the like.

It should be noted that the above description is merely for the convenience of description, but not intended to limit the present disclosure to the scope of the embodiments. It will be appreciated that, after understanding the principle of the present disclosure, those skilled in the art may make various modifications and changes to the form and details of the oxygen production system 100 without departing from the principle of the present disclosure. However, these modifications and changes are not departed from the scope of the present disclosure. In some embodiments, the oxygen production system 100 may further include other components not shown in the figures. For example, a front of the gas inlet port of the compressor may be connected to the air filter. The components may be connected through a valve or a pipeline. A back of the air outlet of the molecular sieve may be connected to a fine sieve tower, a humidifier, a flowmeter, or the like.

Figure 2:
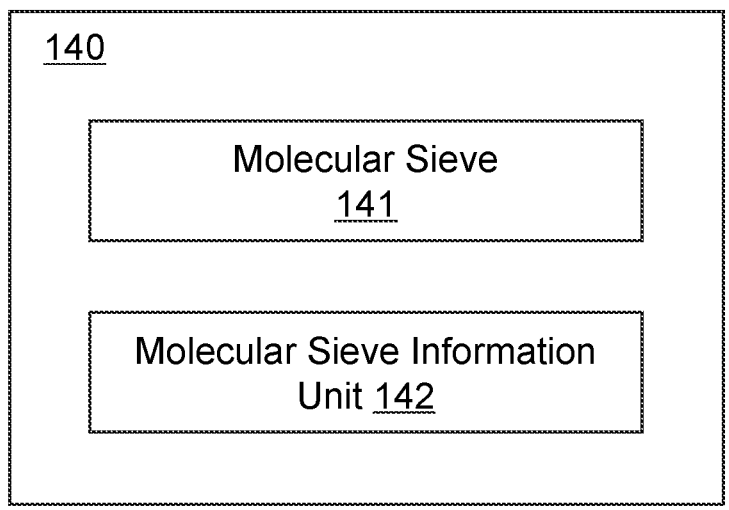
FIG. 2 is a block diagram illustrating an exemplary molecular sieve module according to some embodiments of the present disclosure.

FIG. 2 is a block diagram illustrating an exemplary molecular sieve module according to some embodiments of the present disclosure. The molecular sieve module 140 may include a molecular sieve 141 and a molecular sieve information unit 142.

The molecular sieve 141 may be configured to separate nitrogen and oxygen in compressed air. The molecular sieve 141 may include at least one molecular sieve tower. A zeolite may be filled in each molecular sieve tower as an adsorbent. Since oxygen has a larger quadrupole moment, an acting force between nitrogen and the cation in the zeolite may be stronger. Thus, the zeolite may preferentially adsorb nitrogen, and retain oxygen in the gas phase. The zeolite of the molecular sieve tower may include, but is not limited to, aluminum silicate, LiX, LiAgX, Li-LSX, etc.

The performance of the molecular sieve 141 may gradually decline with the increase of use time. There may be a variety of reasons for the decline in performance. For example, the compressed air entering the molecular sieve 141 may carry dust, oil, or other impurities. The zeolite adsorbent may be contaminated with these impurities for a long time, which reduces the adsorption capacity of the zeolite adsorbent. Therefore, it is necessary to maintain or replace the molecular sieve 141 in time to ensure an oxygen production effect of the oxygen production system 100. Traditional methods rely on manual records or checks. For example, the use time of the molecular sieve may be recorded manually, or whether the molecular sieve has obvious impurities or the performance of the molecular sieve significantly decreases (e.g., whether the maximum oxygen flow significantly decreases compared to a previous or an earlier check) may be regularly checked. This manual method may cost a lot of time and labor, and the molecular sieves may not be maintained or replaced in time because of manual negligence. Especially for a portable oxygen generator such as a home oxygen generator, the user normally does not have awareness and conditions to maintain or check the device from time to time. When the molecular sieve has been used for a long time or an exception occurs to the molecular sieve, the user's experience of using the oxygen generator may be affected greatly. According to some embodiments of the present disclosure, information of the molecular sieve 141 may be automatically recorded by the molecular sieve information unit 142. An accumulated run time or an abnormality of the molecular sieve 141 may be detected automatically, thereby reminding the user to maintain or replace the molecular sieve in time.

The molecular sieve information unit 142 may store information of the molecular sieve 141. In some embodiments, the molecular sieve information unit 142 may store factory information and operation information of the molecular sieve 141. The factory information may include, but is not limited to, a model, an identification, a batch, a component, a design parameter, a design lifetime, a manufacturer, a date of manufacture, and other information. The identification may indicate an identity of the molecular sieve 141. Specifically, each molecular sieve 141 may have its own unique official identification when leaving a factory. The identification may be in various forms, including but not limited to, a string, a barcode, a quick response (QR) code, etc. In some embodiments, the identification may include a code and a factory number. The design lifetime refers to an effective use time to maintain a certain nitrogen-oxygen separation effect, which is predicted by the manufacturer when designing the molecular sieve. The design lifetime may be determined according to an experiment. Merely by way of example, the design lifetime may be 1 year, 2 years, 3 years, 4 years, 5 years, etc. The operation information may include an accumulated run time (i.e., a total time for operating the molecular sieve since the molecular sieve is manufactured), temperature information, operation state information, altitude information, position information, or the like.

In some embodiments, the molecular sieve information unit 142 may store the information of the molecular sieve 141 through an electrically erasable programmable read and write memory (EEPROM). Data in the EEPROM may not be lost after power-off, and the data may be read after power-on again. The manufacturer may store the factory information of the molecular sieve in the EEPROM. In some embodiments, the manufacturer may encrypt the factory information and then store it in the EEPROM. The encrypted data may be not easy to be tampered with.

In some embodiments, the molecular sieve information unit 142 may include a processing chip connected to the EEPROM. The processing chip may read data in the EEPROM, write data into the EEPROM and/or analyze data read from the EEPROM. Specifically, when the molecular sieve information unit 142 is powered (i.e., the oxygen production system 100 is operated), the processing chip may read the data stored in the EEPROM, and write data into the EEPROM during the operation of the oxygen production system 100. In some embodiments, the accumulated run time may be stored in the EEPROM. When the oxygen production system 100 is started each time, the processing chip may retrieve the accumulated run time from the EEPROM, and record a single run time of a current run. The processing chip may obtain an updated accumulated run time by adding the single run time of the current run to the accumulated run time, and then write the updated accumulated run time into the EEPROM. For example, when the oxygen production system 100 is started at one time, the processing chip may read that the accumulated run time stored in the EEPROM is 100 hours, and then record that the single run time of the current run is 2 hours, the processing chip may determine that the update accumulated run time is 102 hours, and write the update accumulated time in the EEPROM. In some embodiments, after the processing chip obtains the accumulated run time and the oxygen production system 100 is started, the updated accumulated run time may be determined every a certain period (e.g., 10 seconds, 20 seconds, 30 seconds, 1 minute, 2 minutes, 3 minutes, 4 minutes, 5 minutes, etc.) by adding the certain period to the accumulated run time, and written into the EEPROM. In some embodiments, the processing chip may encrypt the data and/or information and then write it into the EEPROM. The data and/or information may be encrypted using a variety of encryption algorithms, for example, an asymmetric encryption algorithm, including but not limited to a data encryption standard (DES), a triple data encryption standard (3DES), an advanced encryption standard (AES), etc. As another example, the encryption algorithms may include an asymmetric algorithm, including but not limited to a rivet, shamir, adleman (RSA) algorithm, a digital signature algorithm (DSA), an elliptic curve cryptography (ECC) algorithm, etc. As another example, the encryption algorithms may include a hashing algorithm, including but not limited to a secure hash algorithm 1 (SHA-1), a message-digest algorithm (MD5), etc. The encrypted data may not be easily tampered, which allows the main control module 120 to read accurate molecular sieve data, thereby ensuring the safety and reliability of the oxygen production system 100. In some embodiments, the main control module 120 may also control a communication module (not shown in figures) in the oxygen production system 100 to upload the updated accumulated run time to a cloud server. In some embodiments, the main control module 120 may also be configured to update the temperature information, the operation state, the altitude information, the position information, or the like, or any combination thereof, of the molecular sieve.

It should be noted that, although the above descriptions describe reading data from the EEPROM or writing data into the EEPROM via the processing chip of the molecular sieve 142, in some other embodiments, the main control module 120 may read the data in the EEPROM directly, and analyze the read data, or the main control module 120 may write the data into the EEPROM directly.

The main control module 120 may acquire information in the molecular sieve module 140 (e.g., the molecular sieve information unit 142), and control the operation of the oxygen production system 100 based on the acquired information. In some embodiments, the main control module 120 may control the oxygen production system 100 to perform a corresponding operation in response to at least part of the information of the molecular sieve exceeding a preset range. In some embodiments, the main control module 120 may acquire information of the molecular sieve stored in the molecular sieve module 140 and display it to the user through the interactive module 180. In some embodiments, the main control module 120 may send information acquired from the molecular sieve module 140 to the storage module (not shown in figures) for storage, so that the information is easy to acquire when necessary. For example, the main control module 120 may send the identification of the molecular sieve, the design lifetime, and the accumulated run time obtained from the molecular sieve module 140 to the storage module for storage. When the user needs the information of the molecular sieve (e.g., when the oxygen production system 100 is checked), the information may be obtained to determine if the molecular sieves need to be maintained and/or replaced. In some embodiments, the storage module may also store the user's respiratory state information and/or usage record. For example, the storage module may store a respiratory frequency, an exhalation time, and an inhalation time of the user, and an operation parameter set when the user operates the oxygen production system. The stored information may be used to analyze a healthy condition and a usage habit of the user, and enable the oxygen production system to achieve an automatic adjustment.

In some embodiments, when the oxygen production system 100 is started, the main control module 120 may acquire the design lifetime and the accumulated run time of the molecular sieve, determine whether the accumulated run time exceeds the design lifetime, and control the operation of the oxygen production system 100 based on a determination result. For example, if the accumulated run time does not exceed the design lifetime, the main control module 120 may control the oxygen production system 100 to start and run. If the accumulated run time exceeds the design lifetime, the main control module 120 may control the oxygen production system 100 to perform a reminding operation. In some embodiments, the main control module 120 may control the interactive module 180 to perform the reminding operation, such as displaying alarm information, issuing an alarm sound, lighting an alarm lamp, or the like. As another example, reminding information may be sent to a user terminal (e.g., a mobile phone, a computer, of the user) through a communication module (not shown in figures) in the oxygen production system 100. In some embodiments, if the information acquired from the molecular sieve module 140 is incorrect (e.g., data is abnormally lost, data is rewritten), the main control module 120 may control the oxygen production system 100 (e.g., the interactive module 180) to perform an error reporting operation, and not to start the oxygen production system 100. In some embodiments, for a molecular sieve module manufactured by a particular manufacturer, a molecular sieve information unit of the molecular sieve module may store official information of the molecular sieve. The official information of the molecular sieve may include a unique official identification and other official information (e.g., a model, a batch, a component, a design parameter, a design lifetime, a manufacturer, a date of manufacture, an accumulated use time, etc.). The identity of the molecular sieve may be determined based on the unique official identification, and the other official information of the molecular sieve may also be obtained. In some embodiments, when the user starts the oxygen production system 100, the main control module 120 may read the identification information of the molecular sieve. If the main control module 120 does not acquire the identification information of the molecular sieve, or the information of the molecular sieve read by the main control module 120 does not match the unique official identification, the molecular sieve may be considered to be abnormal, and the oxygen production system 100 may be controlled to stop running and/or perform an error reporting and reminding operation. If the main control module 120 acquires the identification of the molecular sieve, and the information of the molecular sieve read by the main control module matches the unique official identification, the molecular sieve may be considered to be normal. In some embodiments, if the identification information of the molecular sieve read by the main control module does not match the unique official identification, the other information of the molecular sieve may further be obtained. The main control module 120 may determine whether the other information matches the other official information of the molecular sieve corresponding to the unique official identification. If the other information matches the other official information of the molecular sieve corresponding to the unique official identification, the molecular sieve may be considered to be normal. Otherwise, the molecular sieve may be considered to be abnormal. By setting the unique official identification, an imitated or refurbished molecular sieve may be identified effectively, thereby ensuring that the molecular sieve used in the oxygen production system 100 meets the requirements. In some embodiments, when the oxygen production system 100 is in an operation state, the main control module 120 may determine whether the accumulated run time of the molecular sieve exceeds the design lifetime, and control the oxygen production system 100 to perform a corresponding operation according to the determination result. In some embodiments, when the oxygen production system 100 is in the operation state, the main control module 120 may constantly acquire information from the molecular sieve module 140. If the information is incorrect, the oxygen production system 100 may be controlled to stop running.

It should be noted that the above description is merely for the convenience of description, but not intended to limit the present disclosure to the scope of the embodiments. It will be appreciated that, after understanding the principle of the present disclosure, those skilled in the art may modify and change the form and details of the molecular sieve, without departing from the principle of the present disclosure. However, these modifications and changes are not departed from the scope of the present disclosure. For example, in addition to the EEPROM, the molecular sieve information unit 142 may user other non-volatile storage devices, such as a flash memory, a ferromagnetic random-access memory, or the like.

Figure 3:
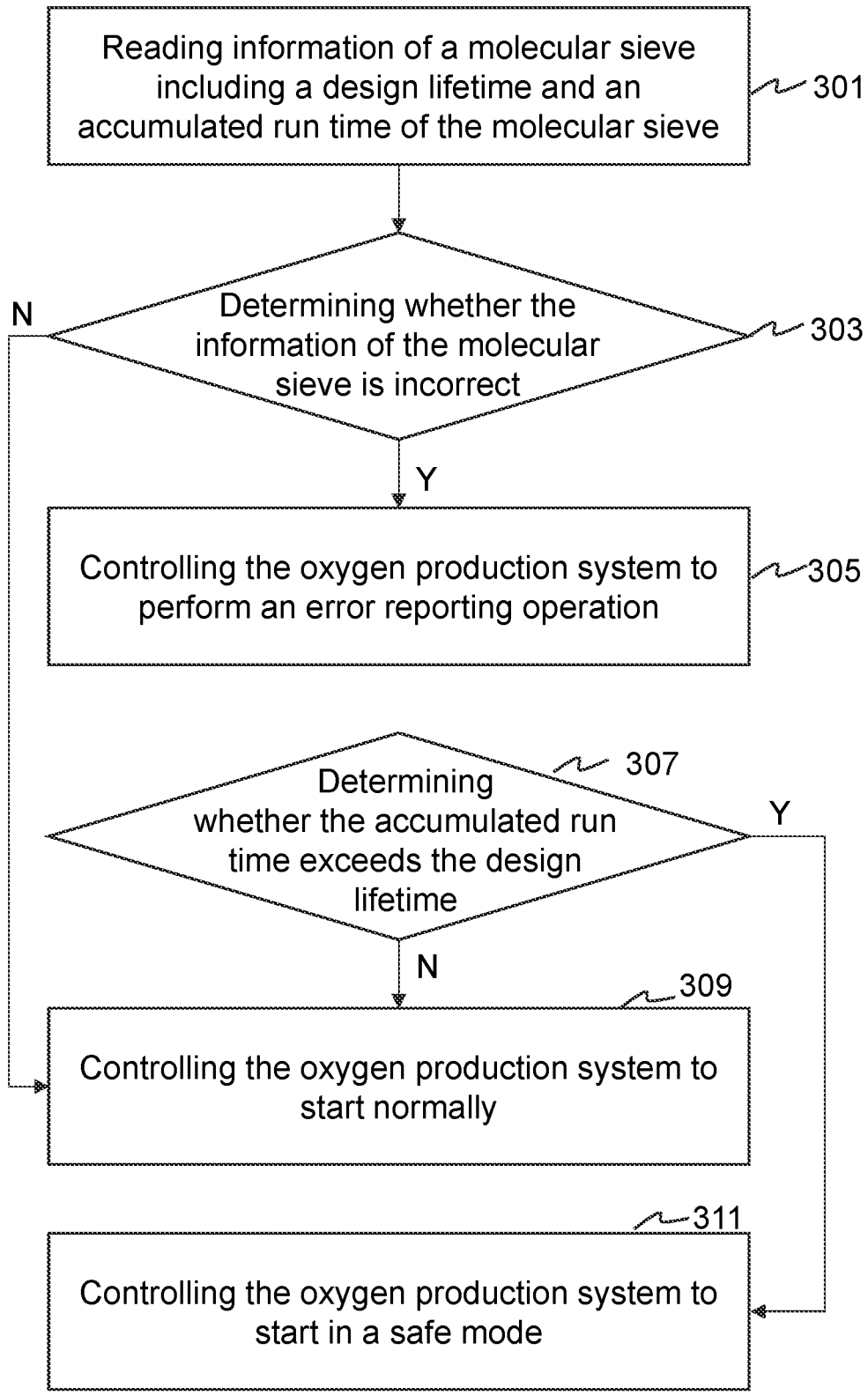
FIG. 3 is a flowchart illustrating an exemplary process for controlling an oxygen production system according to some embodiments of the present disclosure.

FIG. 3 is a flowchart illustrating an exemplary process for controlling an oxygen production system according to some embodiments of the present disclosure. Specifically, process 300 may be performed by the main control module 120.

In 301, information of a molecular sieve may be read. The information of the molecular sieve may include a design lifetime and an accumulated run time of the molecular sieve. Specifically, the main control module 120 may read the information of the molecular sieve when the user starts the oxygen production system 100 (e.g., a user presses a start button). In some embodiments, the main control module 120 may read the information of the molecular sieve from the molecular sieve module 140 (e.g., the molecular sieve information unit 142).

In 303, a determination as to whether the information of the molecular sieve is incorrect may be made. In some embodiments, the molecular sieve information unit 142 may store information in a non-volatile storage device such as an EERPOM. The data stored in the storage device may have errors, for example, data abnormality, data tamper, or data loss. For example, in the case of data loss, the main control module 120 cannot read the information of the molecular sieve, and the information of the molecular sieve may be regarded as being incorrect. In some embodiments, if the information of the molecular sieve indicates that the molecular sieve is not suitable for the corresponding oxygen production system, for example, if the information of the molecular sieve does not match a parameter of other modules in the oxygen production system, the information of the molecular sieve may be considered to be incorrect. If the information of the molecular sieve is incorrect, operation 305 may be performed. Otherwise, operation 307 may be performed.

In 305, in response to determining that the information of the molecular sieve read by the main control module 120 is incorrect, the oxygen production system may be controlled to perform an error reporting operation. In some embodiments, the main control module 120 may control a display module (e.g., an interactive module 180 having a display function) of the oxygen production system to perform the error reporting operation, for example, displaying an error reporting text, an error reporting image, etc. In some embodiments, the main control module 120 may control a vocal module (e.g., an interactive module having a vocal function, a speaker, a buzzer) of the oxygen production system to perform the error reporting operation, for example, issuing an alarming sound. In some embodiments, the main control module 120 may control a light-emitting module (e.g., a light-emitting diode) of the oxygen production system to perform the error reporting operation, such as keeping emitting light or flashing. In some embodiments, the control module 120 may also control a communication module (not shown in figures) of the oxygen production system to send an error reporting and reminding to a user terminal (e.g., a mobile phone, a computer, etc.). Specifically, the communication module may transmit the error reporting and reminding directly to the user terminal, or the communication module may send the error reporting and reminding to a server, and then the server may send the error reporting and reminding to the user terminal.

In 307, in response to the information of the molecular sieve read by the main control module 120 is correct, a determination as to whether the accumulated run time exceeds the design lifetime may be made. If the accumulated run time does not exceed the design lifetime, operation 309 may be performed. Otherwise, operation 311 may be performed.

In 309, in response to determining that the accumulated run time does not exceed the design lifetime, the oxygen production system may be controlled to normally start.

In 311, in response to determining that the accumulated run time exceeds the design lifetime, the oxygen production system may be controlled to start in a safe mode. In some embodiments, the safe mode may be started under the premise of reminding the user. Similar to operation 305 of controlling the oxygen production system to perform the error reporting operation, the main control module may control the display module, the vocal module, and the light-emitting module in the oxygen production system to perform the reminding operation, and control the communication module in the oxygen production system to send an error reporting and reminding to the user terminal. In some embodiments, the safe mode may only allow the oxygen production system to operate for a preset time period, and after the preset time period, the oxygen production system may be forcibly shutdown.

FIGS. 4-8 and FIG. 10 are schematic diagrams illustrating exemplary portions of an oxygen production system according to some embodiments of the present disclosure. The portions may include a gas tank 150, a gas ejection port 160, and a respiratory sensor 172. An oxygen transport pipeline 192 may be provided between the gas tank 150 and the gas ejection port 160. The respiration sensor 172 may be connected to the oxygen transport pipeline 192 through a bypass pipeline 193.

The gas tank 150 may store oxygen. The gas ejection port 160 may connect to the user (e.g., a nasal cavity of the user)

to provide oxygen. The respiratory sensor 172 may detect a respiratory state of the user, for example, whether the user starts inhaling and/or breathing, the user's respiratory frequency, etc. Various forms of respiratory sensors may be used in the present disclosure, including but not limited to, a thermal respiratory sensor, a differential pressure respiratory sensor, a humidity respiratory sensor, or the like. In some embodiments, the respiratory sensor used in the present disclosure may detect the user's breath by detecting a micro-pressure change between exhalation and inhalation or by detecting a change of an inhalation flow.

Figure 4:
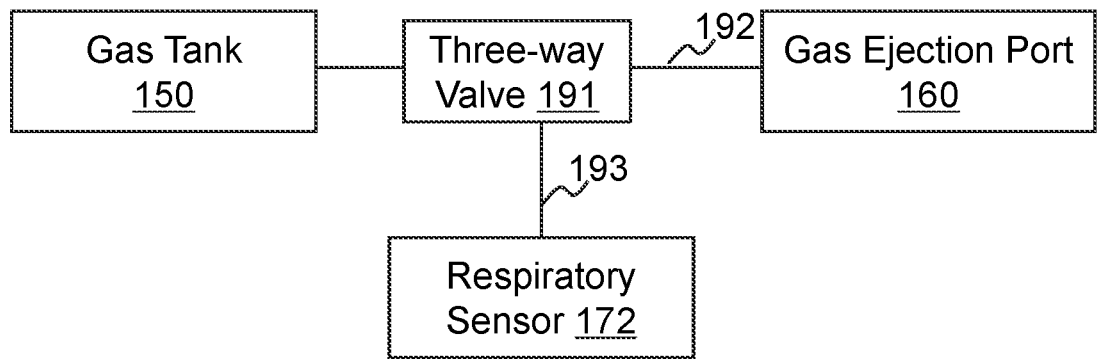
FIG. 4 is a schematic diagram illustrating an exemplary portion of an oxygen production system according to some embodiments of the present disclosure.

In a conventional oxygen generator, a gas tank and a gas ejection port may be connected to an oxygen transport pipeline via a two-way valve. The respiratory sensor may be connected to the oxygen transport pipeline via a bypass pipeline to detect user's breath. This connection method may have following drawbacks: if the gas ejection port is blocked, the pressure in the oxygen transport pipeline and the bypass line may be significantly increased, the respiratory sensor may be subjected to a large pressure, which may damage the respiratory sensor, and the lifetime of the respiratory sensor may be shortened. As shown in FIG. 4, the present disclosure may solve the problem by replacing the two-way valve with a three-way valve.

Figure 5:
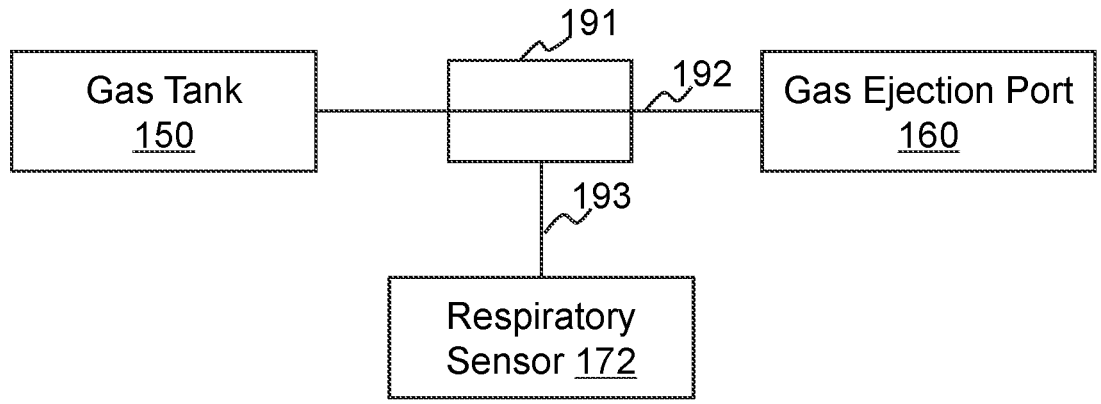
FIG. 5 is a schematic diagram illustrating an exemplary portion of an oxygen production system according to some embodiments of the present disclosure.
Figure 6:
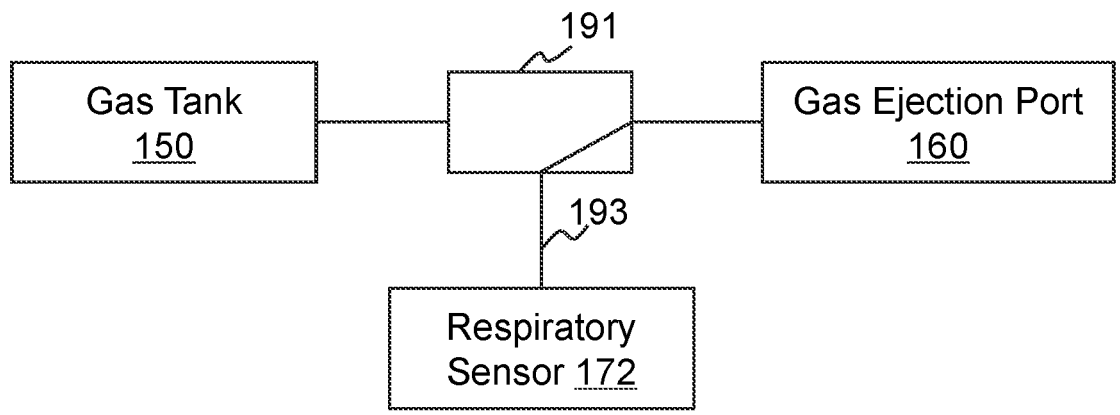
FIG. 6 is a schematic diagram illustrating an exemplary portion of an oxygen production system according to some embodiments of the present disclosure.

In some embodiments, the three-way valve 191 may be a two-position three-way valve having two states. Under the first state, a connection may be established between the gas tank 150 and the gas ejection port 160 as shown in FIG. 5. Under the second state, a connection may be established between the gas ejection port 160 and the respiratory sensor 172 as shown in FIG. 6.

In some embodiments, the respiratory sensor 172 and the three-way valve 191 may be electrically connected to the main control module 120. The main control module 120 may control a connection state of the three-way valve 191 according to the respiratory state of the user detected by the respiratory sensor 172. Specifically, when the oxygen production system 100 is in an initial state to start operating, the three-way valve 191 may connect the gas ejection port 160 and the respiratory sensor 172. The gas tank 150 may not be connected to the gas ejection port 160, and the gas tank 150 may not be connected to the respiratory sensor. Accordingly, the gas ejection port 160 may not provide oxygen to the user (as shown in FIG. 6). When the user starts to inhale, the change in airflow caused by the inhalation may be transmitted from the gas ejection port 160 to the respiratory sensor 172, and the respiratory sensor 172 may thus detect the user's inhalation. At this time, the main control module 120 may control the three-way valve 191 to switch the state so as to connect the gas tank 150 and the gas ejection port 160. At this time, the gas ejection port 160 may provide oxygen to the user (as shown in FIG. 5), while the respiratory sensor 172 may not be connected to the oxygen transport pipeline 192. In some embodiments, another pipeline (not shown in figures) may be provided between the gas ejection port 160 and the respiratory sensor 172, or a pipeline that is directly in contact with the user (e.g., a nasal cavity of the user) may be provided at the end of the respiratory sensor 172, so as to detect the respiratory state of the user when the respiratory sensor 172 is not connected to the oxygen transport pipeline 192. In some embodiments, the main control module 120 may control the three-way valve 191 to connect the gas tank 150 and the gas ejection port 160 at a certain time after the respiratory sensor 172 detects the user's inhalation, and maintain the connection between the gas tank 150 and the gas ejection port 160 for a preset time period. After the preset time period, the three-way valve 191 may be controlled to switch to connect the gas ejection port 160 and the respiratory sensor 172, until a next inhalation of the user is detected, it may be switched back to the state of connecting the gas tank 150 and the gas ejection port 160. The maintained preset time period may be a fixed value, or determined according to an actual required oxygen supply amount and/or a respiratory frequency of the user. For example, in 0.05 seconds after each inhalation of the user, the main control module 120 may control the three-way valve 191 to connect the gas tank 150 and the gas ejection port 160, and maintain the connection between the gas tank 150 and the gas ejection port 160 for 2 seconds. After 2 seconds, the main control module 120 may control the three-way valve 191 to switch to connect the gas ejection port 160 and the respiratory sensor 172. By using such a design of the three-way valve, the respiratory sensor 172 may be isolated from the gas tank 150 under the circumstances that the user does not inhale, which may avoid that the respiratory sensor 172 is subjected to excessive pressure when the gas ejection port 160 is blocked, and the lifetime of the respiratory sensor may be improved. In some embodiments, a flow regulation valve may also be connected to the gas tank 150 for regulating an oxygen output flow. In some embodiments, an oxygen supply valve may be provided on the oxygen supply pipeline 192. An oxygen output time of the oxygen production system may be controlled by turning on or turning off the oxygen supply valve. More descriptions for regulating the oxygen output flow and the oxygen output time may be found in FIG. 8 and the descriptions thereof.

Figure 7:
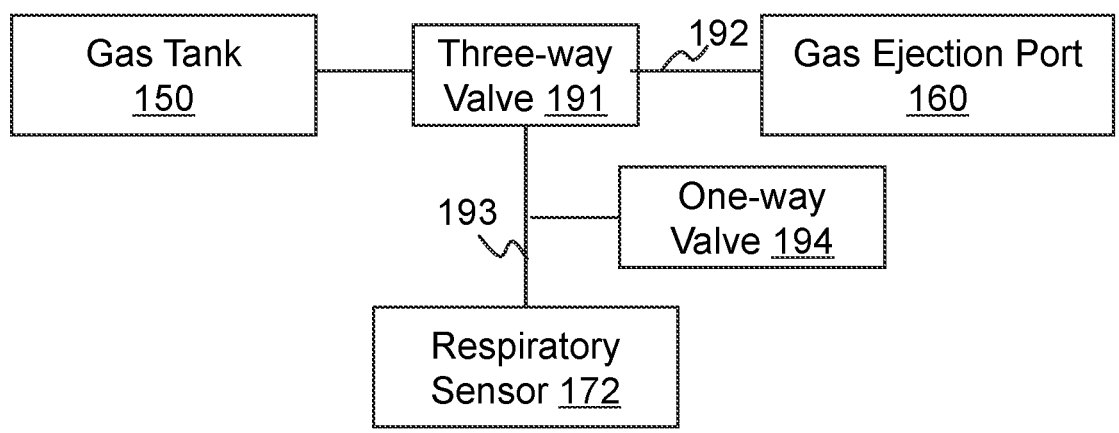
FIG. 7 is a schematic diagram illustrating an exemplary portion of an oxygen production system according to some embodiments of the present disclosure.

In some embodiments, as shown in FIG. 7, a one-way valve 194 may be provided on the bypass pipeline 193. When the oxygen ejection ends, or when the pressure at the respiratory sensor 172 (i.e., the bypass pipeline 193) exceeds a preset pressure threshold, the main control module 120 may control the one-way valve 194 to connect the bypass pipeline 193 and atmosphere, so as to discharge gas in the bypass pipeline 193, thereby avoiding the respiratory sensor 172 from being subjected to excessive pressure. In some embodiments, the preset pressure threshold may be less than or equal to a safety pressure threshold of the respiratory sensor 172, thereby ensuring the safety of the respiratory sensor.

Figure 8:
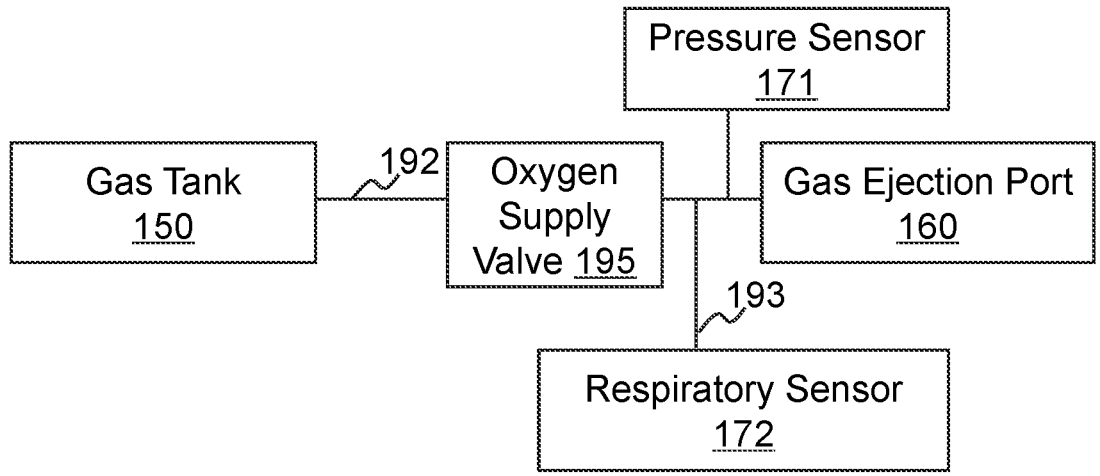
FIG. 8 is a schematic diagram illustrating an exemplary portion of an oxygen production system according to some embodiments of the present disclosure.
Figure 9:
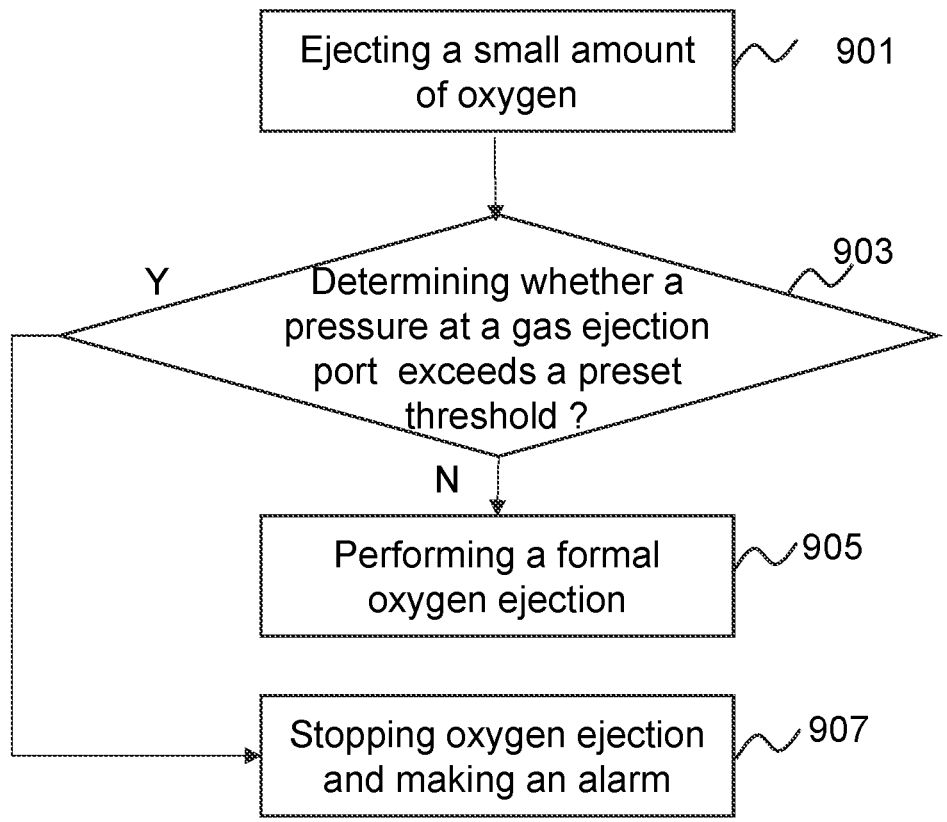
FIG. 9 is a flowchart illustrating an exemplary process for controlling an oxygen production system according to some embodiments of the present disclosure.

In some embodiments, a determination as to whether the gas ejection port is blocked may be determined by ejecting a small amount of oxygen before a formal oxygen ejection, so as to solve the above-mentioned problem of applying excessive pressure on the respiratory sensor 172 due to the blockage of the gas ejection port. As shown in FIG. 8, the oxygen transport line 192 may be provided with an oxygen supply valve 195. The oxygen supply valve 195 may be used to conduct or block the oxygen supply pipeline 192. A pressure sensor 171 may be provided at the gas ejection port 160 and used to detect the pressure at the gas ejection port. FIG. 9 illustrates a workflow of the oxygen production system as shown in FIG. 8.

In 901, a small amount of oxygen may be ejected. Before the formal oxygen ejection, the main control module 120 may control the oxygen supply valve 195 to be turned on, such that the gas tank 150 may eject the small amount of oxygen to the gas ejection port 160. The specific amount of the small amount of oxygen may be preset, for example, 5 ml, 3 ml, 2 ml, 1 ml, etc.

In 903, a determination as to whether the pressure at the gas ejection port exceeds a preset threshold may be made. After the gas tank 150 ejects the small amount of oxygen to the gas ejection port 160, if the pressure sensor 171 detects that the pressure at the gas ejection port 160 exceeds the preset pressure threshold (e.g., 120 kPa, 110 kPa, etc.), or a difference between the pressure at the gas ejection port 160 after the small amount of oxygen is ejected and the pressure at the gas ejection port 160 before the small amount of oxygen is ejected exceeds a preset amplitude threshold (e.g., 50%, 40%, 30%, etc.), it may indicate that the gas ejection port 160 is blocked, and operation 907 may be performed. The main control module 120 may control the oxygen supply valve 195 to block the oxygen supply pipeline 192 so as to stop oxygen injection. If the pressure sensor 171 detects that the pressure at the gas ejection port 160 does not exceed the preset pressure threshold, or the difference between the pressure at the gas ejection port 160 after the small amount of oxygen is ejected and the pressure at the gas ejection port 160 before the small amount of oxygen is ejected does not exceed the preset amplitude threshold, it may indicate that the gas ejection port 160 is not blocked, and operation 905 may be performed. The main control module 120 may control the oxygen supply valve 195 to continue to be turned on to perform the formal oxygen ejection.

Figure 10:
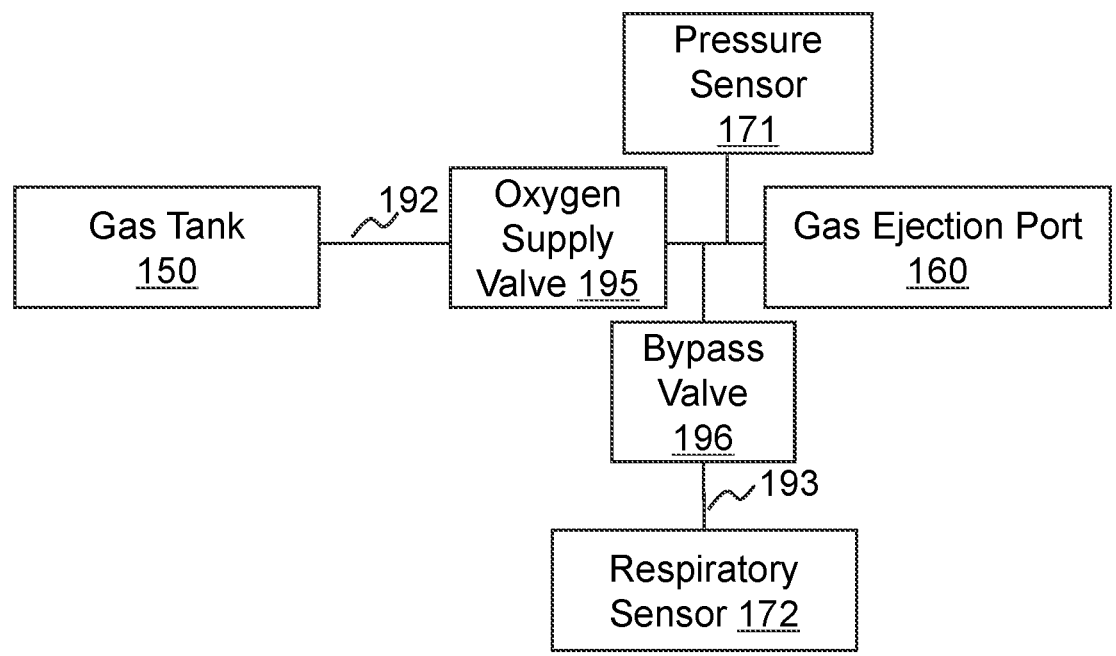
FIG. 10 is a schematic diagram illustrating an exemplary portion of an oxygen production system according to some embodiments of the present disclosure.
Figure 11:
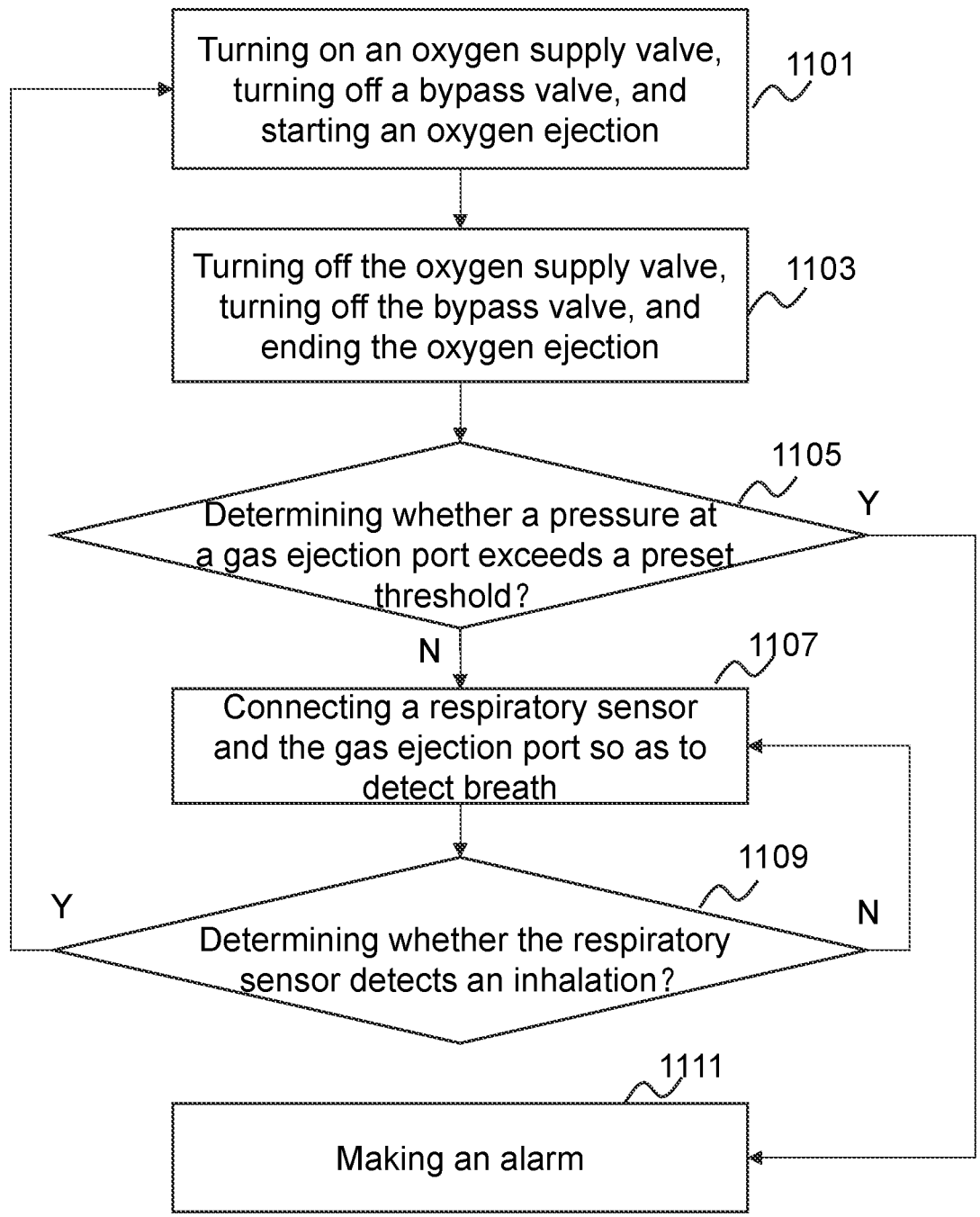
FIG. 11 is a flowchart illustrating an exemplary process for controlling an oxygen production system according to some embodiments of the present disclosure.

In some embodiments, a bypass valve may be provided on the bypass pipeline, so as to solve the above-mentioned problem of applying excessive pressure on the respiratory sensor due to the blockage of the gas ejection port 144. As shown in FIG. 10, the bypass pipeline 193 may be provided with a bypass valve 196. The bypass valve 196 may be used to conduct and block the bypass pipeline 193. A pressure sensor 171 may be provided at the gas ejection port 160 to detect the pressure at the gas ejection port. FIG. 11 illustrates a workflow of the oxygen production system shown in FIG. 10.

In 1101, an oxygen supply valve may be turned on, a bypass valve may be turned off, and an oxygen ejection may be started. During the oxygen ejection, the main control module 120 may control the oxygen supply valve 195 to conduct the oxygen supply pipeline 192, so that the oxygen in the gas tank 150 may reach the gas ejection port 160. The bypass valve 196 may block the bypass pipeline 193 to prevent oxygen from reaching the respiratory sensor 172.

In 1103, the oxygen supply valve may be turned off, the bypass valve may be turned off, and the oxygen ejection may be ended. At the end of the oxygen ejection, the oxygen supply valve 195 may block the oxygen supply pipeline 192.

In 1105, a determination as to whether a pressure at the gas ejection port exceeds a preset threshold may be made. After the oxygen ejection, if the pressure sensor 171 detects that the pressure at the gas ejection port 160 exceeds the preset pressure threshold, it may indicate that the gas ejection port 160 is blocked, and operation 1111 may be performed to make an alarm. In this situation, the bypass valve 196 may be still turned off, and the system may no longer eject oxygen. If the pressure sensor 171 detects that the pressure at the gas ejection port 160 does not exceed the preset pressure threshold, it may indicate that the gas ejection port 160 is not blocked, and then operation 1107 may be performed. The main control module 120 may control the bypass valve 196 to be turned on to connect the respiratory sensor 172 and the gas ejection port 160, so as to detect the user's breath.

In 1109, a determination as to whether the respiratory sensor detects the user's inhalation may be made. If the respiratory sensor detects the user's breath, the process may proceed back to operation 1101, and the oxygen ejection may be started, otherwise, the user's inhalation may be detected.

It should be noted that, in some embodiments, the pressure sensor 171 and the respiratory sensor 172 shown in FIG. 8 and/or FIG. 10 may be the same sensor. For example, when the respiratory sensor 172 is a differential pressure sensor, it may have both breath detection and pressure detection functions.

Figure 12:
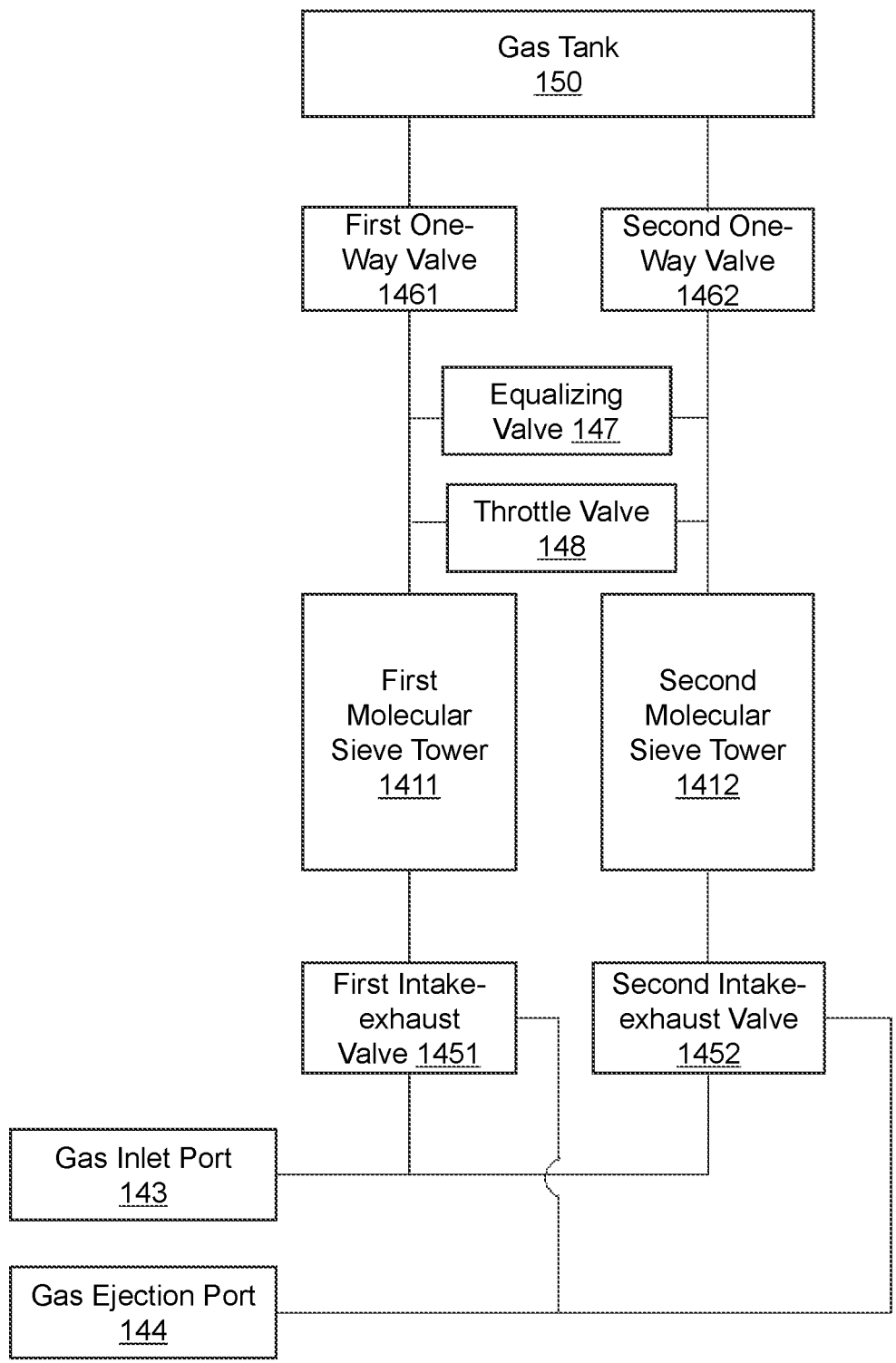
FIG. 12 is a schematic diagram illustrating an exemplary portion of an oxygen production system according to some embodiments of the present disclosure.

FIG. 12 is a schematic diagram illustrating an exemplary portion of an oxygen production system according to some embodiments of the present disclosure.

In some embodiments, the molecular sieve may use a double molecular sieve tower including a first molecular sieve tower 1411 and a second molecular sieve tower 1412. In some embodiments, the two molecular sieve towers may be connected via a pressure equalizing valve 147. The pressure equalizing valve 147 may be used to balance pressures between the two molecular sieve towers. In some embodiments, a throttle valve 148 may be provided between the two molecular sieve towers for controlling a gas flow between the two molecular sieve towers. In some embodiments, a first intake-exhaust valve 1451 and a second intake-exhaust valve 1452 may be two-position three-way valves, each of which may have two states. Under one state, a connection between the gas inlet port 143 and a corresponding molecular sieve tower may be established, and under the other state, a connection between the gas ejection port 144 and the corresponding molecular sieve may be established. In some embodiments, the first intake-exhaust valve 1451 and the second intake-valve 1452 may be rotary solenoid valves. In some embodiments, the first molecular sieve tower 1411 and the second molecular sieve tower 1412 may alternately generate oxygen. When one of the molecular sieve towers generates oxygen, the other molecular sieve tower may desorb nitrogen adsorbed on the molecular sieve tower. Specifically, when the first molecular sieve tower 1411 starts to generate oxygen, the first intake-exhaust valve 1451 may connect the gas inlet port 143 and the first molecular sieve tower 1411. Compressed air may reach the first intake-exhaust valve 1451 through the gas inlet port 143, and enter the first molecular sieve tower 1411. The first molecular sieve tower 1411 may adsorb nitrogen in the compressed air. Oxygen remaining in the gas phase may reach the first one-way valve 1451, and then enter the gas tank 150 for storage. At this time, the second intake-exhaust valve 1452 may connect the second molecular sieve tower 1412 and the gas ejection port 144. The second molecular sieve tower 1412 may desorb nitrogen. The desorbed nitrogen may reach the second intake-exhaust valve 1452, and be discharged from the gas ejection port 144. When the second molecular sieve tower 1412 starts to generate oxygen, the second intake-exhaust valve 1452 may connect the gas inlet port 143 and the second molecular sieve tower 1412. The first intake-exhaust valve 1451 may connect the first molecular sieve tower 1411 and the gas ejection port 144. The first molecular sieve tower 1411 may desorb nitrogen.

At present, manufacturers on the market usually provide molecular sieve towers and valves (e.g., the first intake-exhaust valve 1451, the second intake-exhaust valve 1452, the first one-way valve 1461, the second one-way valve 1462, and the second one-way valve 1462, the pressure equalizing valve 147, and/or the throttle valve 148 as shown in FIG. 7) to the user separately. Users, especially users of a portable oxygen generator, such as a home oxygen generator, toned to purchase and replace the molecular sieve towers and the valves separately, which is costly and inconvenient. If the assembly is improper, the overall performance and effect of the oxygen production system may be affected. The present disclosure solves this problem by integrating the molecular sieve towers and the valves into one piece, and provide the integrated device to the user. In the present disclosure, an integration refers to assembling different components together and providing them to the user as a whole.

In some embodiments, the first intake-exhaust valve 1451 and the second intake-exhaust valve 1452 may be connected to and integrated into the first molecular sieve tower 1411 and the second molecular sieve tower 1412, respectively. In some embodiments, the first intake-exhaust valve 1451 and/or the second intake-exhaust valve 1452 may be a rotary solenoid valve. In some embodiments, the first one-way valve 1461 and the second one-way valve 1462 may be connected to and integrated into the first molecular sieve tower 1411 and the second molecular sieve tower 1412, respectively. In some embodiments, the pressure equalizing valve 147 and/or the throttle valve 148 may be connected to and integrated into the two molecular sieve towers. By integrating the valves and the molecular sieve towers into one piece and providing the integrated device to the user, the integrated replacement of the valves and the molecular sieve towers may be realized, and the structure of the molecular sieve module may be more compact, the occupied space may be reduced, and it may be also convenient for users to purchase and install.

It should be understood that the portion of the oxygen production system shown in FIG. 12 is merely an example, and the present disclosure cannot be limited to the scope of the embodiments. It should be understood that for persons having ordinary skills in the art, under the teachings of the present disclosure, multiple variations and modifications may be made on the form and details of the portion of the oxygen production system. However, those variations and modifications do not depart from the scope of the present disclosure. In some embodiments, the first one-way valve 1461 and the second one-way valve 1462 may be replaced with a three-way valve. In some embodiments, the first intake-exhaust valve 1451 and the second intake-exhaust valve 1452 may be replaced by a two-position five-way valve, and the overall structure may be simpler and more convenient. In addition, it should be understood that a portion connected to the back of the gas tank 150 is not shown in FIG. 10. In some embodiments, the portion connected to the back of the gas tank 150 may be as shown in FIGS. 4-8 and FIG. 10.

Figure 13:
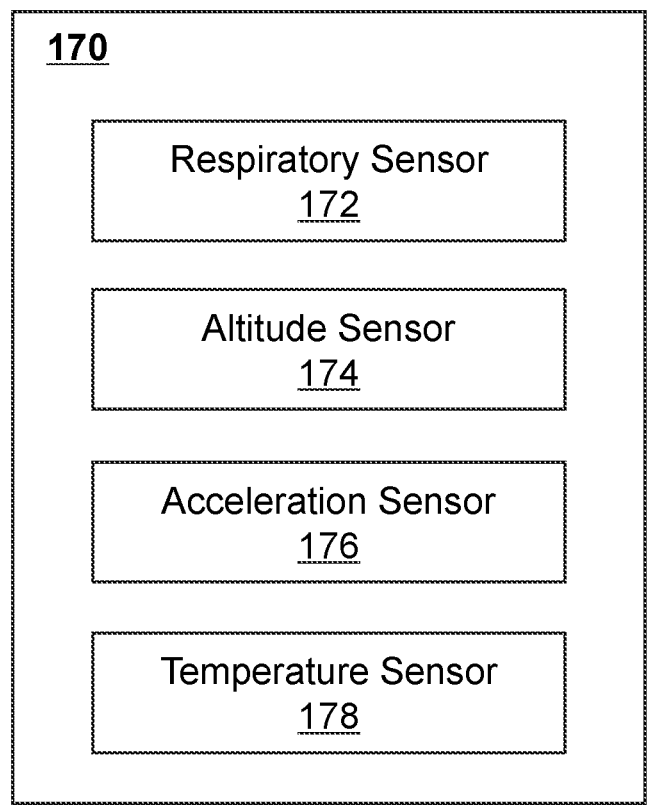
FIG. 13 is a block diagram illustrating an exemplary sensor module of an oxygen production system according to some embodiments of the present disclosure.

FIG. 13 is a block diagram illustrating an exemplary sensor module of an oxygen production system according to some embodiments of the present disclosure. In some embodiments, the sensor module 170 may include a respiratory sensor 172, an altitude sensor 174, a temperature sensor 178, and an acceleration sensor 176. It should be noted that the description of the sensor module 170 in the present disclosure is merely an example, and the present disclosure cannot be limited in the scope of the embodiments. In some embodiments, the sensor module 170 may not include all the sensors listed above. In some embodiments, the sensor module 170 may include the respiratory sensor 172, the altitude sensor 174, the acceleration sensor 176, the temperature sensor 178, or the like, or any combination thereof.

The respiratory sensor 172 may detect the respiratory state of the user, such as whether the user is breathing and/or inhaling, a respiratory frequency of the user, or the like. Various types of respiratory sensors may be used in the present disclosure. In some embodiments, a thermal respiratory sensor may be used. The thermal respiratory sensor may obtain a respiratory signal by detecting a temperature change caused by respiration. In some embodiments, a differential pressure sensor may be used. The differential pressure sensor may obtain the respiratory signal by detecting a pressure change caused by respiration. In some embodiments, a humidity respiratory sensor may be used. The humidity respiratory sensor may obtain the respiratory signal by detecting a humidity change caused by the respiration. In some embodiments, a wearable device attached to the periphery of the chest and the abdomen of the user may be used. The wearable device may obtain the respiratory signal by detecting a physical change of the surface of the chest cavity caused by the respiration.

When a person breathes normally, a volume and a flow rate of gas during exhalation and inhalation may change with the respiratory frequency. The respiratory frequency refers to a count of times the user breaths per unit time. In general, the higher the respiratory frequency is, the shorter a respiratory cycle is, the less the gas volume of a single inhalation or a single exhalation is, the greater the gas flow rate of a single inhalation or a single exhalation is. In some embodiments, the respiratory sensor 172 may detect the respiratory frequency of the user. In some embodiments, the respiratory frequency may be determined based on a count of times the user inhales per minute. In some embodiments, the main control module 120 may control an oxygen output flow based on the respiratory frequency of the user. Specifically, a flow regulation valve may be provided after the gas tank 150, and the oxygen output flow may be adjusted via the flow regulation valve. In some embodiments, the higher the respiratory frequency of the user is, the larger the oxygen output flow controlled by the main control module 120 may be. For example, if the respiratory frequency is 15 times per minute, the oxygen output flow may be 400 milliliters (mL) per minute. If the respiratory frequency is 30 times per minute, the oxygen output flow may be 720 mL per minute. In some embodiments, the main control module 120 may adjust a single oxygen output time according to the respiratory frequency. For example, the faster the respiratory frequency is, the shorter the single oxygen output time may be. Specifically, after the respiratory sensor detects the user's inhalation, the main control module 120 may control the oxygen production system to output oxygen, and maintain the output of oxygen for a preset time. In some embodiments, since the user may have the highest inhalation efficiency during an initial stage of inhalation (e.g., 0.5 seconds, 1 second, 1.5 seconds, etc. after the user starts to inhale), the inhalation efficiency then decreases subsequently, the main control module 120 may control the oxygen production system to output oxygen only during the initial stage of the inhalation (e.g., 0.5 seconds, 1 second, 1.5 seconds, etc. after the user starts to inhale), or control the oxygen production system to output the maximum oxygen output flow in the initial stage of the inhalation, and then the oxygen output flow may gradually decrease. In some embodiments, when the user starts to use the oxygen generation system, the user may manually set an initial oxygen output flow and/or oxygen output time (e.g., via the interactive module 180) according to an individual condition. Then, the respiratory frequency of the user may change, and the oxygen production system may automatically adjust the oxygen output flow and/or the oxygen output time based on the change of the respiratory frequency of the user. In some embodiments, the main control module 120 may adjust the oxygen flow and/or the single oxygen output time according to the respiratory frequency, and at the same time, control a total amount of outputted oxygen within a preset time to be fixed, regardless of the respiratory frequency. For example, the amount of outputted oxygen per minute may be fixed to 1 liter (L).

At present, oxygen generators on the market either eject oxygen all the time, or only eject oxygen when the user inhales. Ejecting oxygen all the time may waste a lot of oxygen, and the efficiency of oxygen ejection may be low. If oxygen is only ejected when the user inhales, at the end of the inhalation, high-concentration oxygen may remain at the end of the gas ejection port. After the high-concentration oxygen is diffused, the oxygen concentration may decrease, and the user may only inhale low-concentration oxygen at the beginning of the next inhalation. In addition, when the user exhales, bacteria may stay at the end of the gas ejection port, and the next time the user inhales or the oxygen generator ejects oxygen, the bacteria may be brought into the nasal cavity of the user.

Usually, it takes a period of time (e.g., 2 seconds, 1.5 seconds, 1 second) after the user exhales and before the user starts the next inhalation. The present disclosure solves the above problems of oxygen concentration reduction and bacterial residue by ejecting a small amount of oxygen (hereinafter referred to as "small amount of oxygen injection") after the end of the user's exhalation and before the start of the next inhalation. Specifically, when the respiratory sensor 172 detects an end of the user's exhalation, the main control module 120 may control the oxygen production system 100 to perform the small amount of oxygen ejection. At this time, only a small amount of oxygen may be ejected, for example, 10 ml, 5 ml, or 3 ml, or oxygen may be continuously ejected for a short time, for example, 1 second or 0.5 seconds, or the amount of ejected oxygen may only account for a set proportion of a normal amount of outputted oxygen, for example, 80%, 70%, 60%, 50%, 30%, to ensure that the small amount of oxygen ejection is merely performed before the next inhalation. In some embodiments, in the small amount of oxygen ejection, the amount of oxygen ejected by the gas ejection port each time, or the duration of each oxygen ejection may be determined according to the respiratory frequency of the user. Specifically, the higher the respiratory frequency of the user is, the shorter an interval between the end of one exhalation and the beginning of the next inhalation may be. Therefore, the amount of ejected oxygen may be decreased, and the duration of oxygen injection may be reduced. After the small amount of oxygen ejection, if the respiratory sensor 172 detects the user's inhalation, the main control module 120 may control the oxygen production system to eject oxygen normally. If the respiratory sensor 172 does not detect the user's inhalation, the oxygen production system may not eject oxygen any more. If the respiratory sensor 172 detects the user's inhalation in the small amount of oxygen ejection, the main control module 120 may control the oxygen production system to switch from the small amount of oxygen ejection to a normal oxygen ejection. By using the small amount of oxygen injection, high-concentration oxygen may be remained at the gas ejection port after the user finishing each exhalation, and be inhaled by the user in the next inhalation. At the same time, the residual bacteria at the end of the gas ejection port may be discharged, so as to avoid the health hazards caused by the inhalation of the bacteria in the next inhalation, or the injection of these bacteria into the nasal cavity of the user by the oxygen generation system in the next oxygen ejection.

The altitude sensor 174 may detect an altitude of the oxygen production system. Various types of altitude sensors may be used in the present disclosure. In some embodiments, an air pressure-based altitude sensor may be used. In some embodiments, a global position system (GPS)-based altitude sensor may be used. Generally, the higher the altitude is, the less oxygen is, and more oxygen is needed. The main control module 120 may control the oxygen output flow and/or the oxygen output time based on the altitude. In some embodiments, the higher the altitude is, the longer the oxygen output time may be. In some embodiments, the higher the altitude is, the greater the total amount of oxygen outputted in a time period may be. For example, the higher the altitude is, the greater the amount of oxygen outputted per minute may be. In some embodiments, the higher the altitude is, the greater the oxygen output flow may be. In some embodiments, the user may manually set an initial oxygen output flow and/or an initial oxygen output time according to an actual situation when starting using the oxygen production system. Then the altitude of the user may change, and the oxygen production system may automatically adjust the oxygen output flow and/or the oxygen output time based on the change of the altitude.

The acceleration sensor 176 may acquire acceleration data to determine a current motion state of the user. Various types of acceleration sensors may be used in the present disclosure, including but not limited to, a piezoelectric acceleration sensor, a piezoresistive sensor, a capacitive sensor, a servo sensor, or the like. In some embodiments, the acceleration sensor 176 may be provided in the oxygen production system 100. The oxygen production system 100 may move with the movement of the user. Therefore, acceleration data measured by the acceleration sensor 176 may reflect the motion state of the user. In some embodiments, the acceleration sensor 176 may be disposed on the user. For example, the acceleration sensor 176 may be disposed on a wearable device (e.g., a bracelet, a watch, a belt, glasses, a helmet, etc.) of the user. In this situation, the acceleration sensor 176 may obtain the acceleration data of the user directly. In general, the acceleration of each action when a person is in a vigorous motion is greater than that when the person is in a non-vigorous motion. For example, the acceleration of a step when a person is running fast is greater than that when he is walking. Therefore, the motion state of the user may be determined based on the acceleration data. In some embodiments, the main control module 120 may qualitatively determine the motion state of the user according to the acceleration data of the user, such as determine whether the user is walking or running. In some embodiments, the main control module 120 may qualitatively determine the motion state of the user (e.g., a vigorous motion state, a medium-intensity motion state, a calm state) by determining whether an acceleration value exceeds a preset threshold. In some embodiments, at least one acceleration threshold may be set, and the motion state of the user may be determined by determining whether the acceleration value of the user exceeds a corresponding acceleration threshold. In some embodiments, the main control module 120 may quantitatively determine the motion state of the user (e.g., the intensity of the motion of the user) according to the acceleration data of the user. Specifically, the larger the acceleration value is, the more intense the user's motion may be. In some embodiments, the acceleration sensor 176 may be a three-axis acceleration sensor, which may simultaneously detect the acceleration in three dimensions perpendicular to each other. The motion state of the user may be determined by analyzing the acceleration in the three dimensions using at least one human motion state recognition algorithm. The human motion state recognition algorithm may include but is not limited to, an autoregressive model algorithm, a pattern matching algorithm, a clustering algorithm, etc. In some embodiments, a neural network model may be trained using known acceleration and known human motion state data. The trained model may determine the motion state of the user according to the acceleration data.

In general, the more intense the motion is, the higher the respiratory frequency may be, the shorter a single exhalation time may be, the less an amount of oxygen in a single inhalation may be, but the greater a total amount of oxygen inhaled within a same time period may be. Therefore, the oxygen output flow and/or the oxygen output time may be determined according to the motion state of the user. In some embodiments, the oxygen output flow and/or the oxygen output time of the oxygen production system may be controlled by the main control module 120. Specifically, the more intense the motion is, the shorter the oxygen output time may be. As another example, the more intense the motion is, the larger the total amount of oxygen outputted in a period of time may be. As still another example, the more intense the motion is, the larger the oxygen output flow may be. In some embodiments, if the motion state of the user is qualitatively determined, different motion states may correspond to different amounts of outputted oxygen. For example, an amount of outputted oxygen in a single oxygen output in the calm state may be 30 ml, an amount of the outputted oxygen in the single oxygen output in the medium-intensity motion state may be 27 ml, and an amount of the outputted oxygen in the single oxygen output in the vigorous motion state may be 24 ml. As another example, the total amount of outputted oxygen per minute in the calm state may be 400 ml, the total amount of outputted oxygen per minute in the medium-intensity motion state may be 500 ml, and the total amount of outputted oxygen per minute in the vigorous motion state may be 720 ml. In some embodiments, if the intensity of the motion of the user is qualitatively determined, the amount of outputted oxygen of the oxygen production system may be adjusted accordingly. For example, the oxygen output time may be negatively correlated with the intensity of the motion, the total amount of outputted oxygen in a time period may be positively correlated with the intensity of the motion, and the oxygen output flow may be positively correlated with the intensity of the motion.

In some embodiments, a pressure sensor may be provided in the gas tank 150 of the oxygen production system to detect an air pressure in the gas tank 150. The main control module 120 may adjust the oxygen output flow and/or the oxygen output time according to the air pressure in the gas tank 150. In some embodiments, the larger the air pressure in the gas tank 150 is, the greater the oxygen output flow may be. In some embodiments, the larger the air pressure in the gas tank 150 is, the longer the oxygen output time may be.

It should be noted that the description of adjusting the amount of oxygen outputted by the oxygen production system according to the data detected by the respiratory sensor 172, the altitude sensor 174, and the acceleration sensor 176 are merely embodiments, and the present disclosure cannot be limited to the scope of the embodiments. Other types of sensors may also be used in the present disclosure, and the amount of outputted oxygen may be adjusted according to the data detected by the sensors. For example, the other types of sensors may include a pulse sensor, a blood oxygen concentration sensor, or the like. The higher the pulse frequency is, the greater the oxygen output flow may be, and the shorter the oxygen output time may be.

The lower the blood oxygen concentration is, the greater the oxygen output flow may be. In some embodiments, the data acquired by the various types of sensors may be integrated to control the amount of oxygen outputted by the oxygen production system. In some embodiments, the oxygen output flow and/or the oxygen output time of the oxygen production system may be determined by an artificial intelligence technique. For example, the oxygen output flow and/or the oxygen output time may be determined by a neural network model. Specifically, an input of the neural network model may be data acquired by various sensors, and an output of the neural network model may be data relating to the amount of oxygen outputted by the oxygen production system. The neural network model may be trained using known data of various sensors. The trained neural network model may be used to obtain the data relating to the amount of outputted oxygen based on the data acquired by the various sensors. For example, the respiratory frequency, the respiratory state, the motion state, and the altitude of the user, the air pressure in the gas tank, or other data, of the oxygen production system, the oxygen output flow and/or the oxygen output amount adjusted by the user may be collected. The collected data may be used to train the neural network. The input of the model may be the respiratory frequency, the respiratory state, the motion state, and the altitude of the user, and the air pressure in the gas tank. An output of the model may be the amount of outputted oxygen. The trained model may determine an appropriate oxygen output flow and/or oxygen output time based on the respiratory frequency, the respiratory state, the motion state, and the altitude of the user, and the air pressure in the gas tank. Further, a customize personalized adjustment scheme may be made for a specific user according to a usage habit of the user. For example, an outputted oxygen adjustment model of the specific user may be obtained by training the neural network model using historical usage data of the specific user. In some embodiments, the oxygen output flow and/or the oxygen output time of the oxygen production system may be determined by a machine identification method. For example, a mapping relationship between a detection value of each sensor and the oxygen output flow and/or the oxygen output time may be preset. The appropriate oxygen output flow and/or oxygen output time may be determined based on the detection value of each sensor in an actual situation and the mapping relationship. In some embodiments, the oxygen output flow and/or the oxygen output time of the oxygen production system may be determined by a cloud processing method. For example, a corresponding algorithm (e.g., the neural network model, the mapping relationship) may be preset on a cloud server. The oxygen production system may upload the detection value of the sensor to the cloud server, and the cloud server may determine the appropriate oxygen output flow and/or oxygen output time based on the detection value of the sensor.

The temperature sensor 178 may detect a temperature. In some embodiments, the temperature sensor 178 may be provided on the molecular sieve module 140 (e.g., the molecular sieve 141) for detecting the temperature of the molecular sieve. In some embodiments, the temperature sensor 179 may be integrated into the molecular sieve module 140. In some embodiments, the molecular sieve module 140 may include a cooling fan (not shown in figures) for dissipating heat for the molecular sieve 141 to ensure a good effect of the molecular sieve 141. In some embodiments, the main control module 120 may adjust a rotation speed of the cooling fan based on the temperature of the molecular sieve detected by the temperature sensor 178. In some embodiments, when the temperature of the molecular sieve exceeds a first preset threshold, the main control module 120 may control the cooling fan to increase the rotation speed. When the temperature of the molecular sieve is lower than a second preset threshold, the main control module 120 may control the cooling fan to reduce the rotation speed or stop operation. For example, when the temperature of the molecular sieve exceeds 50 degrees Celsius, the rotation speed of the cooling fan may be controlled to increase. When the temperature of the molecular sieve is less than 25 degrees Celsius, the rotation speed of the cooling fan may be controlled to decrease. In some embodiments, when the temperature of the molecular sieve is too high or too low, and the continuous operation of the oxygen production system may cause serious damage to the molecular sieve. At this time, the oxygen production system may be forced to stop. Specifically, if the temperature of the molecular sieve exceeds a third preset threshold or less than a fourth preset threshold, the main control module 120 may control the oxygen production system to stop operating. The third preset threshold may be greater than the first preset threshold, and the fourth preset threshold may be smaller than the second preset threshold. In some embodiments, the main control module 120 may also determine whether the duration of the temperature of the molecular sieve exceeding the third preset threshold or lower than the fourth preset threshold exceeds a preset time threshold. Only when the duration exceeds the preset time threshold, the oxygen production system may be forced to stop operating. For example, when the duration of the temperature of the molecular sieve exceeding 100 degrees Celsius or lower than 0 degrees Celsius exceeds 4 seconds, the oxygen production system may be forced to stop operating. In some embodiments, after the main control module 120 controls the oxygen production system to stop operating, the main control module 120 may prompt the user. For example, an interface indicating that the system stops operating may be displayed, a prompt sound may be emitted (e.g., by the interactive module 180), a reminding light may be lighted up or flashed, or reminding information may be sent to a user terminal.

In some embodiments, the cooling fan may be connected to a field programmable gate array (FPGA). The FPGA may receive an instruction sent by the main control module (e.g., the main control module 120), and adjust the rotation speed of the cooling fan according to the instruction. Specifically, the control module may acquire the temperature of the molecular sieve detected by the temperature sensor 178, determine a required rotation speed of the cooling fan at the temperature, and transmit data associated with the required rotation speed to the FPGA. The FPGA may send a corresponding clock frequency and a corresponding square wave with a duty cycle to the cooling fan according to the required rotation speed, and adjust a pulse width modulation (PWM) of the cooling fan, thereby adjusting the rotation speed of the cooling fan.

The present disclosure may also provide a mask including the oxygen production system as described above. The user may obtain oxygen conveniently by wearing the mask.

The benefits of the embodiments of the present disclosure may include, but are not limited to the following descriptions. (1) By storing the factory information and the operation information of the molecular sieve in the molecular sieve information unit, the system may determine the state of the molecular sieve according to the factory information and the operation information, and promptly remind the user to maintain or replace the molecular sieve, thereby ensuring the performance and effect of the oxygen production system. (2) By setting a suitable valve between the gas tank, the gas ejection port, and the respiratory sensor, and a state of the valve may be switched based on an inhalation state or a non-inhalation state of the user and the pressure at the gas ejection port, which may avoid a large amount of gas gathering at the respiratory sensor for a long time, so as to avoid damaging the respiratory sensor due to excessive pressure when the gas ejection port is blocked. (3) By integrating the molecular sieve towers and the valves into one piece and provide the integrated device for a user, the user may replace the molecular sieve conveniently, which may ensure the performance and the effect of the oxygen production system after the replacement of the molecular sieve. In addition, the integrated molecular sieve module may have a compact structure, which may reduce space occupation. (4) The environmental data or the state data of the user may be collected by various types of sensors. The amount of oxygen outputted by the oxygen production system may be adjusted based on the data collected by the various types of sensors. The efficiency of the oxygen production system may be improved, and humanized experience may be provided for the user. It should be noted that different embodiments may have different beneficial effects. In different embodiments, the possible beneficial effects may be any one or a combination of the above, or any other beneficial effects that may be obtained.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements, and amendments to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, "one embodiment," "one embodiment," and/or "some embodiments" mean a certain feature, structure, or characteristic related to at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, some features, structures, or features in the present disclosure of one or more embodiments may be appropriately combined.

In addition, those skilled in the art can understand that various aspects of the present disclosure can be illustrated and described through several patentable categories or situations, including any new and useful processes, machines, products, or combinations of materials, or any new and useful improvements. Accordingly, all aspects of the present disclosure may be performed entirely by hardware, may be performed entirely by software (including firmware, resident software's, microcode, etc.), or may be performed by a combination of hardware and software. The above hardware or software's may be referred to as "data block", "module", "engine", "unit", "component" or "system". In addition, aspects of the present disclosure may appear as a computer product located in one or more computer-readable media, the product including computer-readable program code.

The computer storage medium may contain a propagated data signal containing a computer program code, for example, on baseband or as part of a carrier wave. The propagated signal may have multiple manifestations, including electromagnetic form, optical form, etc., or a suitable combination form. The computer storage medium may be any computer-readable medium other than the computer-readable storage medium, and the medium may be connected to an instruction execution system, device, or device to communicate, propagate, or transmit a program for use. Program encoding on a computer storage medium may be propagated by any suitable medium, including radio, cable, fiber optic cable, RF, or a similar medium, or a combination of the above media.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

We claim:

1. An oxygen production system including a main control module and a molecular sieve module, wherein:
   the molecular sieve module includes a molecular sieve and a molecular sieve information unit, and the molecular sieve information unit is configured to store information of the molecular sieve, wherein the molecular sieve is connected with at least one valve, the molecular sieve and the at least one valve are integrated in the molecular sieve module, and the molecular sieve and the at least one valve are integrally replaced;
   the main control module is configured to read, write, and/or update the information of the molecular sieve stored in the molecular sieve information unit; wherein, when reading,
   in response to at least part of the information of the molecular sieve exceeding a preset range, the main control module controls the oxygen production system to perform a corresponding operation.

2. The oxygen production system of claim 1, wherein the information of the molecular sieve includes at least one of design lifetime information, an accumulated run time, temperature information, operation state information, altitude information, or position information of the molecular sieve.

3. The oxygen production system of claim 2, wherein:
   in response to the accumulated run time exceeding the design lifetime, the main control module controls the oxygen production system to perform a reminding operation.

4. The oxygen production system of claim 2, wherein the main control module is configured to:
   update at least one of the accumulated run time, the temperature information, the operation state information, the altitude information, or the position information, and
   write updated information of the molecular sieve into the molecular sieve information unit, wherein the main control module updates the accumulated run time according to a run time of each run of the molecular sieve.

5. The oxygen production system of claim 1, wherein the molecular sieve information unit stores official information of the molecular sieve when the molecular sieve module leaves a factory, and the official information includes at least one of a unique official identification or other official information;
   the main control module is configured to read the at least one of the identification information or other information of the molecular sieve from the molecular sieve information unit;
   the main control module controls the oxygen production system to stop running and perform a reminding operation, in response to at least one of following situations including:
   the identification information of the molecular sieve is not read;
   identification information of the molecular sieve read by the main control module does not match the unique official identification;
   the identification information of the molecular sieve read by the main control module matches the unique official identification, but the other information of the molecular sieve does not match the other official information.

6. The oxygen production system of claim 1, wherein the molecular sieve information unit includes at least one of following storage devices: an electrically erasable programmable read and write memory, a radio frequency memory, a wireless memory, an optical disk, or a magnetic disk.

7. The oxygen production system of claim 1, wherein the information of the molecular sieve is encrypted and stored in the molecular sieve information unit.

8. The oxygen generating system of claim 1, wherein
   the oxygen production system further includes a gas tank, a gas ejection port, and a respiration sensor, the respiration sensor is configured to detect a user's breath, an oxygen transport pipeline is provided between the gas tank and the gas ejection port, and the respiration sensor is connected to the oxygen transport pipeline through a bypass pipeline.

9. The oxygen production system of claim 8, wherein a joint between the oxygen transport pipeline and the bypass pipeline is provided with a two-position three-way valve, and the two-position three-way valve connects the gas ejection port and the respiration sensor at an initial moment when the oxygen production system is activated;

the main control module is also configured to control a connecting state of the two-position three-way valve, wherein:

in response to the respiration sensor detecting a user's inhalation, the main control module controls the two-position three-way valve to connect the gas tank and the gas ejection port, and maintains the connection between the gas tank and the gas ejection port for a preset time;

after the preset time, the main control module controls the two-position three-way valve to connect the gas ejection port and the respiration sensor.

10. The oxygen production system of claim 9, wherein the bypass pipeline is provided with a one-way valve, and the main control module is configured to:

after the preset time, control the one-way valve to connect the bypass pipeline with the atmosphere to discharge a gas in the bypass pipeline; or in response to a pressure at the respiration sensor exceeding a preset pressure threshold, control the one-way valve to connect the bypass line with the atmosphere to discharge the gas in the bypass line.

11. The oxygen production system of claim 8, wherein the oxygen supply pipeline is provided with an oxygen supply valve for conducting or blocking the oxygen supply pipeline, and the gas ejection port is provided with a pressure sensor for detecting a pressure at the gas ejection port.

12. The oxygen production system of claim 11, wherein the main control module is also configured to control the oxygen supply valve to be turned on before a formal oxygen ejection, such that the gas tank outputs a preset amount of oxygen to the gas ejection port; after the gas tank outputs the preset amount of oxygen to the gas ejection port, in response to the pressure sensor detecting that the pressure at the gas ejection port exceeds the preset pressure threshold, the main control module controls the oxygen supply valve to block the oxygen supply pipeline to stop an oxygen ejection;

in response to the pressure sensor detecting that the pressure at the gas ejection port does not exceed the preset pressure threshold, the main control module controls the oxygen supply valve to continue to be turned on to perform the formal oxygen ejection.

13. The oxygen production system of claim 11, wherein the bypass pipeline is provided with a bypass valve for conducting or blocking the bypass pipeline;

during an oxygen ejection, the main control module controls the oxygen supply valve to be turned on to conduct the oxygen supply pipeline, and the bypass valve blocks the bypass pipeline;

at the end of an oxygen supply, the main control module controls the oxygen supply valve to block the oxygen supply pipeline, and, in response to the pressure sensor detecting that the pressure at the gas ejection port exceeds the preset pressure threshold, controls the bypass valve to continue blocking the bypass pipeline;

in response to the pressure sensor detecting that the pressure at the gas ejection port does not exceed the preset pressure threshold, controls the bypass valve to be turned on so that the respiration sensor detects the user's breath.

14. The oxygen production system of claim 1, wherein the oxygen production system further includes:

a temperature sensor configured to detect a temperature of the molecular sieve, the temperature sensor being integrated in the molecular sieve; and a cooling fan configured to dissipate heat for the molecular sieve, the main control module is configured to control the oxygen production system according to the temperature of the molecular sieve, wherein:

in response to the temperature of the molecular sieve exceeding a first preset threshold, the main control module controls the cooling fan to increase a rotation speed;

in response to the temperature of the molecular sieve being lower than a second preset threshold, the main control module controls the cooling fan to reduce the rotation speed.

15. The oxygen production system of claim 14, wherein the main control module is further configured to:

in response to the temperature of the molecular sieve exceeding a third preset threshold or lower than a fourth preset threshold, control the oxygen production system to stop running.

16. The oxygen generating system of claim 1, wherein the oxygen production system further includes at least one of a respiration sensor, an acceleration sensor, an altitude sensor, or a pressure sensor, the respiration sensor is configured to detect a respiratory frequency and/or a respiratory state of a user, the acceleration sensor is configured to detect a motion state of the user, the altitude sensor is configured to detect an altitude of the oxygen production system, the pressure sensor is configured to detect a pressure in a gas tank of the oxygen production system;

the main control module is configured to adjust at least one of an oxygen output flow or an oxygen output time according to at least one of the respiratory frequency, the respiratory state, the motion state of the user, the altitude, or the pressure in the gas tank;

the at least one of the oxygen output flow or the oxygen output time is determined by at least one of an artificial intelligence method, a machine recognition method, or a cloud processing method;

the artificial intelligence method is implemented by a neural network model, an input of which includes at least one of the respiratory rate, the respiratory state, the motion state of the user, the altitude, or the pressure in the gas tank, and an output of which include the at least one of the oxygen output flow or the oxygen output time.

17. The oxygen production system of claim 1, wherein the oxygen production system further includes a gas ejection port for ejecting oxygen and a respiration sensor for detecting a respiratory state of a user;

in response to the respiration sensor detecting an end of the user's exhalation, the main control module controls the gas ejection port to eject a preset amount of oxygen.

18. A mask, wherein the mask includes an oxygen production system, and the oxygen production system includes a main control module and a molecular sieve module, wherein:
- the molecular sieve module includes a molecular sieve and a molecular sieve information unit, and the molecular sieve information unit is configured to store information of the molecular sieve, wherein the molecular sieve is connected with at least one valve, the molecular sieve and the at least one valve are integrated in the molecular sieve module, and the molecular sieve and the at least one valve are integrally replaced;
- the main control module is configured to read, write, and/or update the information of the molecular sieve stored in the molecular sieve information unit; wherein, when reading,
- in response to at least part of the information of the molecular sieve exceeding a preset range, the main control module controls the oxygen production system to perform a corresponding operation.

* * * * *